United States Patent [19]
Roessler et al.

[11] Patent Number: 5,405,342
[45] Date of Patent: Apr. 11, 1995

[54] DISPOSABLE ABSORBENT ARTICLE WITH FLUSHABLE INSERT

[75] Inventors: Thomas H. Roessler, Menasha; Annamaria Cesco-Cancian, Appleton; Dan D. Endres, Appleton; Paula M. Hanson, Appleton; Kenneth A. Leick, Appleton; Marianne K. Leick, Appleton; Edward E. Werner, Oshkosh, all of Wis.

[73] Assignee: Kimberly-Clark Corporation, Neenah, Wis.

[21] Appl. No.: 268,862

[22] Filed: Jun. 29, 1994

Related U.S. Application Data

[63] Continuation of Ser. No. 188,626, Jan. 27, 1994, abandoned, which is a continuation of Ser. No. 116,822, Sep. 3, 1993, abandoned, which is a continuation of Ser. No. 816,457, Dec. 31, 1991, abandoned.

[51] Int. Cl.$^6$ ............................................. A61F 13/15
[52] U.S. Cl. .................................. 604/364; 604/385.1; 604/394; 604/397
[58] Field of Search ...................... 604/364, 385.1, 386, 604/387, 391, 393, 394, 396, 397, 398

[56] References Cited

U.S. PATENT DOCUMENTS

| | | |
|---|---|---|
| 771,001 | 9/1904 | Campbell . |
| 1,133,945 | 3/1915 | Farkas . |
| 1,674,600 | 6/1928 | MacKenzie . |
| 1,931,357 | 10/1933 | Potwin . |
| 2,002,368 | 5/1935 | Fancher . |
| 2,122,417 | 7/1938 | Fridolph . |
| 2,450,059 | 9/1948 | Rickerson . |
| 2,450,789 | 10/1948 | Frieman . |
| 2,530,647 | 11/1950 | Buchler . |
| 2,538,758 | 1/1951 | Bricmont . |
| 2,627,858 | 2/1953 | Miller . |
| 2,649,859 | 8/1953 | Hermanson et al. . |
| 2,688,328 | 9/1954 | Marcus . |
| 2,733,715 | 2/1956 | Folk . |
| 2,893,393 | 7/1959 | Pressley . |
| 3,049,124 | 8/1962 | Thompson . |
| 3,050,063 | 8/1962 | Margraf . |
| 3,110,312 | 11/1963 | Wirth . |
| 3,131,693 | 5/1964 | Gray et al. . |
| 3,162,196 | 12/1964 | Salk . |
| 3,211,147 | 10/1965 | Pherson et al. . |
| 3,364,931 | 1/1968 | Hirsch . |
| 3,430,629 | 3/1969 | Murphy . |
| 3,561,447 | 2/1971 | Alexander . |
| 3,595,235 | 7/1971 | Jespersen . |
| 3,602,225 | 8/1971 | Wielicki . |
| 3,616,797 | 11/1971 | Champaigne, Jr. et al. . |
| 3,635,221 | 1/1972 | Champaigne, Jr. . |
| 3,636,952 | 1/1972 | George . |
| 3,654,928 | 4/1972 | Duchane . |

(List continued on next page.)

FOREIGN PATENT DOCUMENTS

| | | |
|---|---|---|
| 2048214 | 7/1992 | Canada . |
| 0140471 | 5/1985 | European Pat. Off. . |
| 0243013 | 10/1987 | European Pat. Off. . |
| 3343622 | 6/1985 | Germany . |
| 1456428 | 11/1976 | United Kingdom . |
| 2256803 | 12/1992 | United Kingdom . |
| 2269999 | 3/1994 | United Kingdom . |
| WO8911842 | 12/1989 | WIPO . |
| 90/03156 | 4/1990 | WIPO . |
| WO9108722 | 6/1991 | WIPO . |
| 91-10413 | 7/1991 | WIPO . |
| 91/16871 | 11/1991 | WIPO . |

Primary Examiner—Randall L. Green
Assistant Examiner—Mary Beth Jones
Attorney, Agent, or Firm—Thomas M. Gage

[57] ABSTRACT

A disposable article, such as a diaper, for absorbing and containing urine and other body exudates has an absorbent insert pad that may be flushed in a toilet. The article preferably includes a backing sheet and a bodyside liner that are substantially coterminous. In one embodiment of the invention, a secondary absorbent body, which is disposed between the backing sheet and the bodyside liner, has a pocket formed therein. The absorbent insert pad is positioned against the bodyside liner and located generally within the pocket. A cover is releasably attached to the bodyside liner to maintain the insert pad within the pocket.

18 Claims, 11 Drawing Sheets

U.S. PATENT DOCUMENTS

| | | | |
|---|---|---|---|
| 3,665,923 | 5/1972 | Champaigne, Jr. | |
| 3,667,466 | 6/1972 | Ralph | |
| 3,693,621 | 9/1972 | Jarusik et al. | |
| 3,727,615 | 4/1973 | Duchane | |
| 3,741,212 | 6/1973 | Schutte | |
| 3,777,759 | 12/1973 | Oehmke et al. | |
| 3,804,092 | 4/1974 | Tunc | |
| 3,838,695 | 10/1974 | Comerford et al. | |
| 3,874,385 | 4/1975 | Gellert | |
| 3,926,189 | 12/1975 | Taylor | |
| 3,952,745 | 4/1976 | Duncan | |
| 4,019,517 | 4/1977 | Glassman | |
| 4,022,210 | 5/1977 | Glassman | |
| 4,072,150 | 2/1978 | Glassman | |
| 4,244,368 | 1/1981 | Caradonna | |
| 4,265,245 | 5/1981 | Glassman | |
| 4,335,722 | 6/1982 | Jackson | |
| 4,340,563 | 7/1982 | Appel et al. | 264/518 |
| 4,355,722 | 6/1982 | Jackson | 604/364 |
| 4,388,075 | 6/1983 | Mesek et al. | 604/385 |
| 4,405,297 | 9/1983 | Appel et al. | |
| 4,496,360 | 1/1985 | Joffe et al. | 604/397 |
| 4,578,073 | 3/1986 | Dysart et al. | 604/397 |
| 4,585,448 | 4/1986 | Enloe | 604/378 |
| 4,597,760 | 7/1986 | Buell | 604/397 |
| 4,597,761 | 7/1986 | Buell | 604/397 |
| 4,657,802 | 4/1987 | Morman | 428/152 |
| 4,681,577 | 7/1987 | Stern et al. | 604/378 |
| 4,685,915 | 8/1987 | Hasse et al. | 604/378 |
| 4,701,176 | 10/1987 | Wilson | 604/385 A |
| 4,704,116 | 11/1987 | Enloe | 604/385 A |
| 4,747,846 | 5/1988 | Boland et al. | 604/38 A |
| 4,753,649 | 6/1988 | Pazdernik | 604/389 |
| 4,756,709 | 7/1988 | Stevens | 604/385 A |
| 4,798,603 | 1/1989 | Meyer et al. | 604/378 |
| 4,834,735 | 5/1989 | Alemany et al. | 604/368 |
| 4,834,736 | 5/1989 | Boland et al. | 604/385.2 |
| 4,834,737 | 5/1989 | Khan | 604/385.2 |
| 4,846,823 | 7/1989 | Enloe | 604/385.2 |
| 4,846,825 | 7/1989 | Enloe et al. | 604/385.1 |
| 4,861,652 | 8/1989 | Lippert et al. | 428/284 |
| 4,892,598 | 1/1990 | Stevens et al. | 156/91 |
| 4,916,005 | 4/1990 | Lippert et al. | 428/192 |
| 4,938,754 | 7/1990 | Mesek | 604/385.2 |
| 4,955,880 | 9/1990 | Rodriquez | 604/393 |
| 4,964,857 | 10/1990 | Osborn | 604/395 |
| 4,968,312 | 11/1990 | Khan | 604/388.1 |
| 5,026,363 | 6/1991 | Pratt | 604/385.1 |
| 5,026,364 | 6/1991 | Robertson | 604/385.1 |
| 5,108,385 | 4/1992 | Snyder | 604/397 |
| 5,176,672 | 1/1993 | Bruemmer et al. | 604/385.1 |

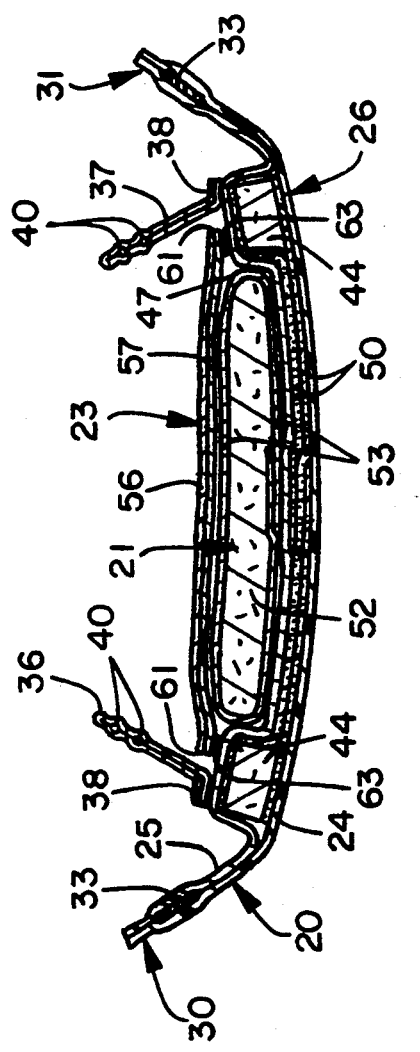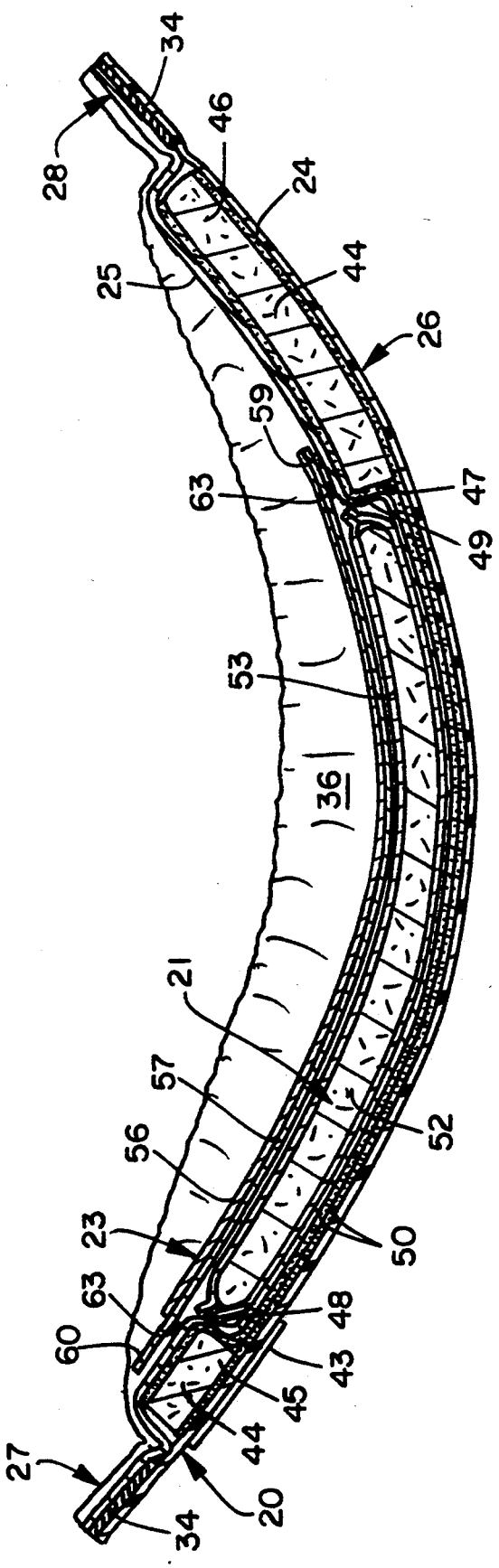

DISPOSABLE ABSORBENT ARTICLE WITH FLUSHABLE INSERT

This is a continuation of application Ser. No. 08/188,626, filed on Jan. 27, 1994, now abandoned, which is a continuation of Ser. No. 08/116,822, filed on Sep. 3, 1993, abandoned, which is a continuation of Ser. No. 07/816,457, filed on Dec. 31, 1991, abandoned.

BACKGROUND OF THE INVENTION

The present invention relates generally to the field of disposable articles utilized for absorption and containment of urine and other body exudates. More particularly, the invention relates to a disposable article, for example a diaper, that incorporates components such as an absorbent insert pad which may be removed from the article and flushed down a toilet.

Disposable articles for the absorption and containment of urine and other body exudates are generally known in the art. Such disposable articles have found particular utility in the fields of infant care, child care, feminine care, and adult incontinency. Present commercially available disposable articles for such uses are generally unitary, preshaped or prefolded, and comprised of a fluid pervious bodyside liner, a fluid impervious backing sheet, and an absorbent material disposed between the bodyside liner and the backing sheet. Disposable articles of this type effectively and efficiently absorb and contain urine or other body exudates. Such articles are designed for a single use and are simply deposited after use in a waste receptacle. This ease and convenience of disposal has contributed to the increasing popularity of such disposable absorbent articles.

Until now, the vast majority of the absorbent articles of the aforementioned type have been designed to be disposed of by delivery to solid waste landfills. Such absorbent articles have not generally been compatible with being flushed clown a toilet. The relatively few products that have been designed specifically to be disposed of, at least partially, by flushing have been ineffective or impractical.

With regard to diapers, for example, U.S. Pat. No. 3,211,147 to P. O. Pherson et al. discloses a diaper pad that is intended to be completely disposed of in household toilets and septic tanks. The pad includes a paper web, several fluff pads, and paper reinforcing strips. The diaper employs numerous channels to distribute fluids. Because the pad contains only wood pulp derivatives, the user may separate the diaper into pieces and flush the pieces in a toilet.

A diaper with a flushable portion is disclosed in U.S. Pat. No. 3,667,466 to H. J. Ralph. This patent discloses a diaper having a flushable layer and a reusable retainer. The flushable layer is composed of top and bottom layers of wet-strength material that surround an absorbent layer. The diaper incorporates numerous perforations which cause the diaper to be self-segmenting and self-disintegrating when immersed in a toilet.

Another diaper with a flushable portion is disclosed in U.S. Pat. No. 4,964,857 to C. Osborn. This patent discloses a diaper that incorporates a removable and flushable inner sheet of material. The inner sheet has a liquid permeable layer, an absorbent layer, and a moisture repellent layer. The inner sheet, which is attached to the remainder of the diaper by adhesives, is constructed with a plurality of perforations and a series of hollow channels. A drawstring located within the channels is used to remove the inner sheet from the remainder of the diaper.

These attempts to provide diapers that are completely or partially flushable have not been entirely successful. For example, the above-mentioned completely flushable diapers must necessarily be limited to materials that can be flushed. Consequently, completely flushable diapers have provided less than desirable fit and absorbency characteristics. On the other hand, the diapers having a flushable layer and a reusable retainer are frequently messy and inconvenient. Finally, the diapers that incorporate a removable insert have not effectively utilized the absorbent material contained within the insert and have tended to prematurely experience saturation spots. Consequently, these diapers have not provided an adequate amount of comfort and dryness. Additionally, these diapers have included devices such as drawstrings to remove the inserts. Devices of this type present numerous manufacturing difficulties and increase the expense and complexity of production.

The present invention teaches an improved disposable article which provides components, such as an absorbent insert pad, which may be quickly and conveniently removed from the article. The user can dispose of the insert pad, as well as any solid feces material held in the article, in any toilet that is connected to a holding tank, a municipal sewer, or other municipal wastewater treatment system. The insert pad may then be flushed down the toilet, and the remainder of the article may be composted or recycled where suitably equipped facilities are available, disposed at a conventional landfill site, or incinerated. Alternately, the complete absorbent article including the insert pad may be directed into the solid waste stream. Thus, the user may select among several alternative disposal methods, thereby accommodating the individual's preferences and the community's capabilities.

SUMMARY OF THE INVENTION

The present invention was developed in order to remedy the previously-mentioned drawbacks associated with present disposable absorbent articles comprising portions that are intended to be flushed down a toilet. It was also developed to allow users of disposable absorbent articles to select among several disposal options, based upon their particular preferences and circumstances. An absorbent article according to the present invention includes a shell with a top surface and an opposite bottom surface. The shell defines a front waist section, a back waist section, and opposed first and second sides extending between the front and back waist sections. A pair of containment flaps are positioned inboard of the respective first and second sides and extend between the front and back waist sections. An insert pad of the article is formed of flushable absorbent material and positioned against the top surface of the shell, between the containment flaps. The insert pad is releasably maintained against the top surface of the shell. Thus, this aspect of the invention gives the user a convenient option to disposing of the article at a conventional landfill site. The absorbent insert pad, as well as the firm fecal waste from the article, can be easily removed from the article and disposed of in a toilet. The insert pad is formed of materials that will disperse in water in conjunction with the hydraulic action of the toilet and the transportation system en route to the treatment facility. In this way, the user has the option of directing the solid fecal waste and a significant portion of the absorbent article to a wastewater treatment facility, rather than to a landfill.

In another aspect of the invention, the absorbent article includes a secondary absorbent body disposed between top and bottom surfaces of a shell. The secondary absorbent body is formed with a pocket. An insert pad is formed of a flushable absorbent material and sized to fit generally within the pocket. The insert pad is positioned against the top surface and releasably maintained within the pocket. This aspect of the invention enhances the leakage protection of the article. The insert pad functions as the initial and primary absorbent of the article. The secondary absorbent body laterally surrounds the insert pad and absorbs liquids which may migrate from the crotch of the article toward the edges of the article.

In another aspect, the absorbent article of the present invention includes a backing sheet and a bodyside liner that define a front waist section, a back waist section, and sides therebetween. A pair of containment flaps extend between front and back waist sections of the article and are positioned inward of the sides. A secondary absorbent body formed with a pocket is disposed between the backing sheet and the bodyside liner, and an insert pad is releasably maintained on the top surface between the containment flaps. This aspect also results in an absorbent article with improved leakage-resistance. The containment flaps retard the movement of solid fecal material, urine, and fluidic fecal material away from the insert pad. The effectiveness of the insert pad is thereby enhanced, which causes the vast majority of the fluidic waste to be absorbed by the insert pad. Where the insert pad is disposed of in a toilet and subsequently flushed, the majority of the fluidic waste of the user is directed to a wastewater treatment facility, rather than to a landfill.

In another aspect of the invention, the absorbent article includes a shell with a secondary absorbent body disposed between top and bottom surfaces of the shell. A removable insert pad, formed of flushable, absorbent material, is positioned against the top surface and is in substantially direct fluid contact with the secondary absorbent body. This aspect of the invention also enhances the leakage protection of the article. The insert pad functions as the initial and primary absorbent structure of the article. Before any particular portion of the absorbent insert pad becomes saturated, however, the secondary absorbent body is available to absorb urine and other fluidic material. The transport of liquid from any particular portion of the absorbent insert pad to the underlying secondary absorbent body is possible because the insert pad and secondary body are in substantially direct fluid contact. Consequently, the insert pad tends not to experience premature saturation spots, and the top surface of the shell and the top of the insert pad remain dry and comfortable for the wearer.

In yet another aspect, the invention includes a method for improved disposal of body exudates, such as urine and solid fecal waste. The method includes providing an absorbent article with a shell and a removable insert pad that is made of materials that separate in water. The shell includes a secondary absorbent body that includes a pocket. The insert pad is located on the shell and generally within the pocket. The method also includes arranging the absorbent article on the body of a wearer in a position where the insert pad receives body exudates from the wearer, removing the insert pad and exudates from the absorbent article, and depositing them in a toilet. The insert pad and exudates are then flushed down the toilet. This aspect of the invention results in solid and liquid waste from the article being disposed of in a toilet. This reduces the amount of non-flushable waste that the user needs to store until it can be entered into the solid waste stream. Correspondingly, this also reduces the odor problems associated with temporarily storing absorbent articles containing solid and liquid human waste.

As can be seen from the foregoing comments, it is an object of the invention to provide an absorbent article that gives the user several disposal options by including a removable portion that can be flushed in a toilet. The removable, flushable portion disperses into fibers or particles that can be accommodated by residential holding tanks or municipal sewers, or treated at municipal wastewater treatment facilities.

It is another object of the invention to provide a disposable absorbent article that facilitates a user's ability to dispose of solid fecal waste in the toilet. The steps involved in removing the insert pad from the article provide a clean and convenient means for removing fecal waste from the article. This beneficially reduces the amount of odor-causing waste that must be stored in the user's residence.

It is another object of the invention to provide an absorbent article that incorporates a relatively thin, removable, flushable insert pad and concurrently offers considerable leakage protection. The non-flushable portion of the article can be constructed of non-flushable materials that are particularly suited to enhance leakage protection.

It is a further object of the invention to provide an absorbent article incorporating a flushable insert portion that can be removed from the article without exposing the user to the soiled portions of the article.

It is still another object of the invention to provide a disposable article having a non-flushable portion and a removable, flushable insert, where the majority of the absorbent material of the article is contained in the flushable insert.

The foregoing and other objects, features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

BRIEF DESCRIPTION OF THE DRAWINGS

FIG. 4 is an enlarged view in section taken generally from the plane of the line 4—4 of FIG. 1.

FIG. 5 is an enlarged view in section taken generally from the plane of the line 5—5 of FIG. 1.

DETAILED DESCRIPTION OF THE PREFERRED EMBODIMENTS

Figure 1:
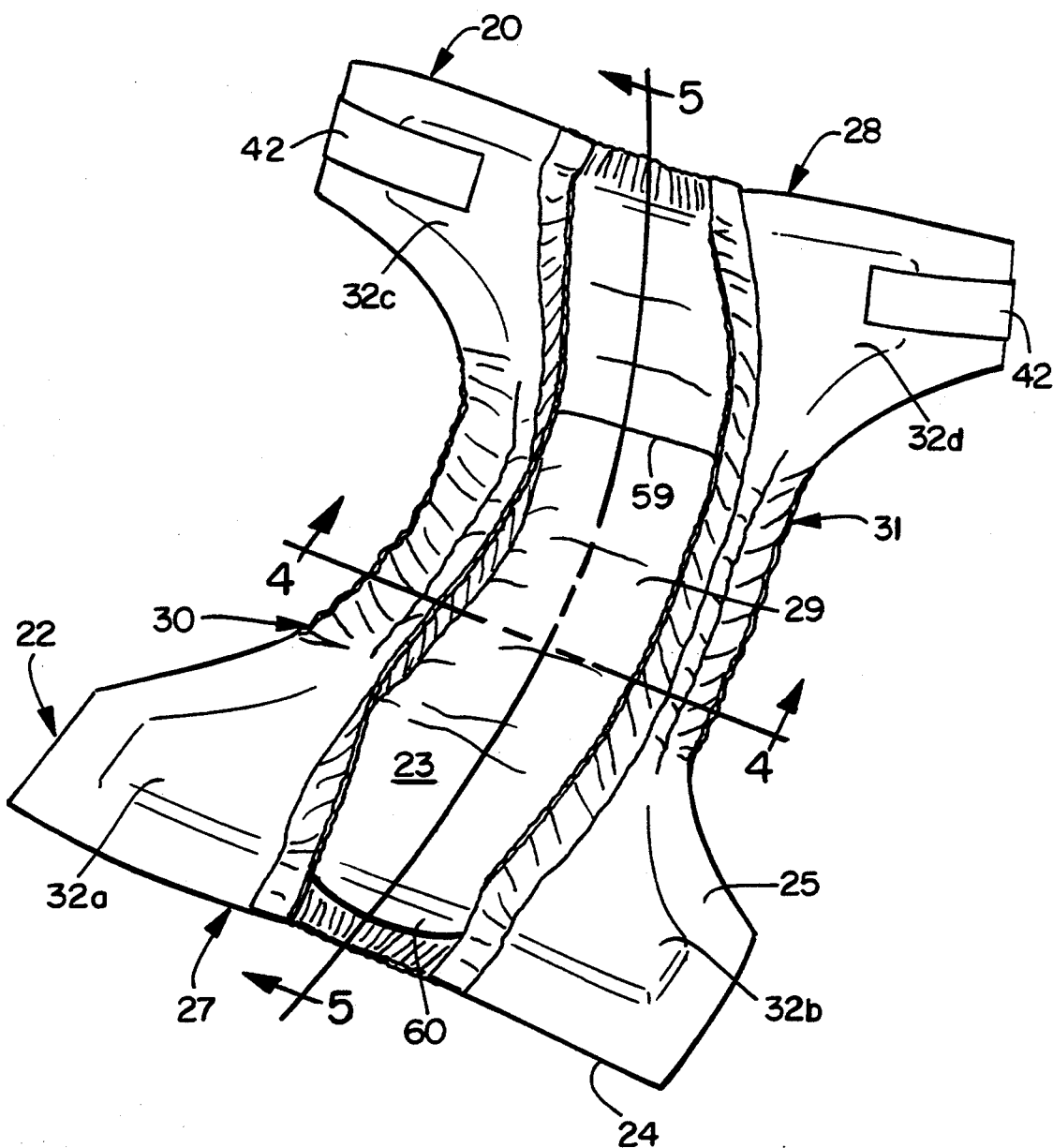
FIG. 1 is a perspective view of a disposable diaper, as an example of an absorbent article according to the present invention.
Figure 2:
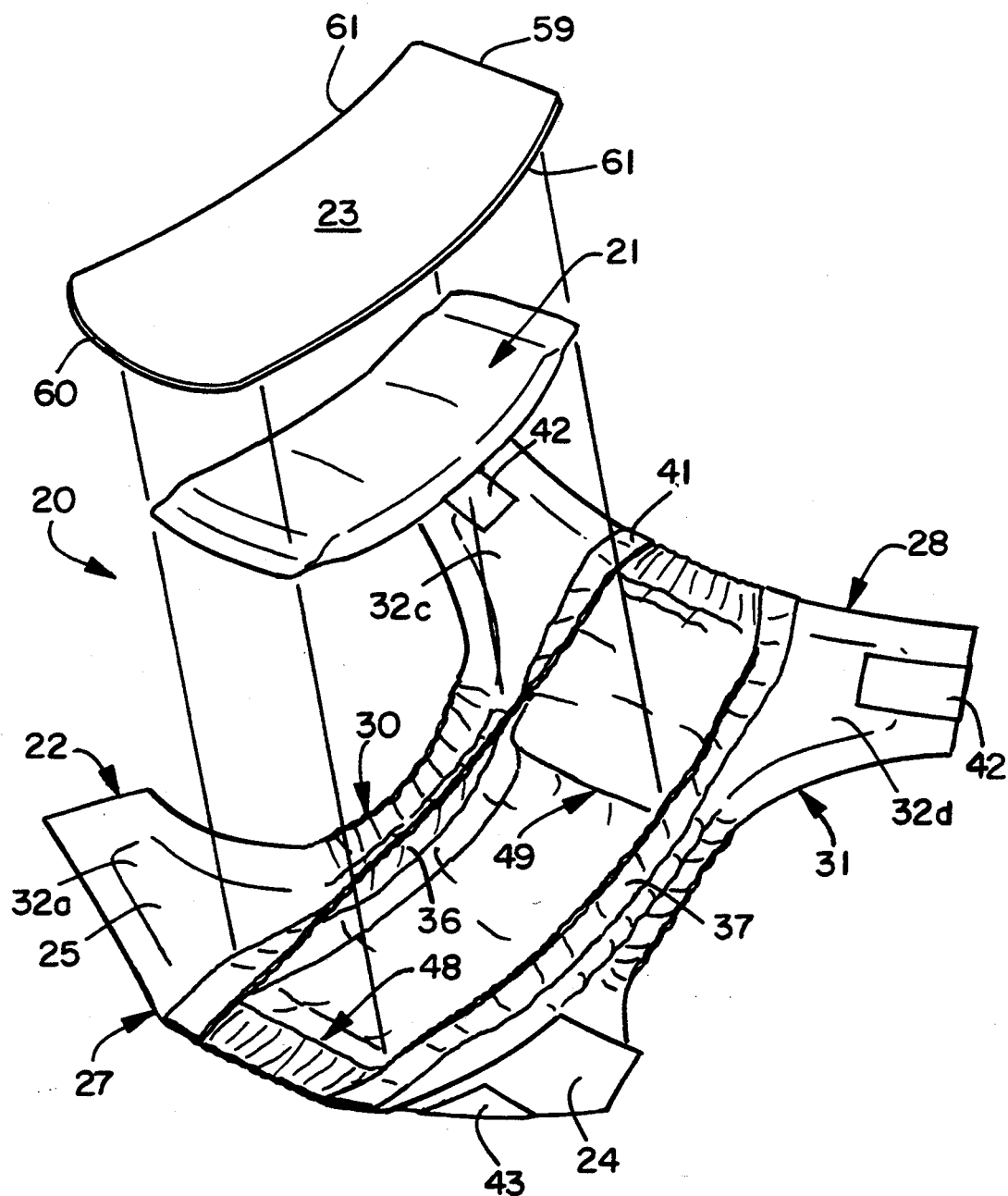
FIG. 2 is an exploded perspective view showing several components of the absorbent article of FIG. 1.

With reference to FIGS. 1 and 2, a disposable absorbent article formed according to the invention is shown for purposes of illustration as a disposable diaper 20. The invention may also be incorporated, however, in absorbent articles such as adult incontinency garments, feminine napkins, children's training pants, or the like. The diaper 20 provides disposal options principally because it includes an absorbent insert pad 21 (FIG. 2) that may be discarded into a toilet that is operatively connected to a holding tank, a municipal sewer, or other types of municipal wastewater treatment systems. The diaper 20 provides other benefits because it enhances a parent's ability to dispose human waste in the toilet.

When encountering the water in the toilet, the insert 21 partially or completely disintegrates into individual, flushable fibers. Upon flushing the insert pad 21 and any fecal waste, remaining undisintegrated portions of the pad 21 disperse due to hydraulic action while exiting the bowl or en route to a municipal sewer or wastewater treatment facility. Thus, a diaper 20 incorporating the present invention gives users the option of conveniently directing their child's bodily waste, along with disintegrative and treatable portions of the diaper, to a wastewater treatment facility. The remaining portions of the diaper 20 that are not flushed are suitable for recycling, composting or solid waste disposal, according to the user's preference and the availability of appropriate facilities.

In general, a disposable diaper 20 incorporating the present invention is formed of a non-flushable garment shell 22, a flushable absorbent insert pad 21 positioned adjacent to and in contact with the shell, and a non-flushable cover 23 for releasably maintaining the insert pad in position relative to the shell. It will be understood, however, that presently non-flushable components of the diaper, such as the cover 23, may also be formed of flushable materials.

The shell 22 preferably comprises a substantially liquid impervious backing sheet 24 and a substantially liquid pervious bodyside liner 25 that are in facing relation and substantially coterminous. A secondary absorbent layer 26 (see FIGS. 3–5), discussed more fully below, is employed in the illustrated embodiment and is disposed between the backing sheet 24 and the bodyside liner 25.

More specifically, the backing sheet 24 may comprise a thin, substantially liquid impermeable web or sheet of plastic film such as polyethylene, polypropylene, polyvinyl chloride or similar material. The backing sheet 24 may also be formed of a compostable material such as a web or sheet of polyvinyl alcohol-based film. The backing sheet material may be transparent or opaque and have an embossed or matte surface. One preferred material for the backing sheet 24 is a polyethylene film that has a nominal thickness of about 0.00125 inch and a systematic matte embossed pattern, and that has been corona treated on both sides. Alternately, the backing sheet 24 may comprise a nonwoven, fibrous web which has been suitably constructed and arranged to be substantially liquid impermeable.

The bodyside liner 25 may be any soft, flexible, porous sheet which passes fluids therethrough. The bodyside liner 25 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The bodyside liner 25 has a pore size that readily allows the passage therethrough of liquids, such as urine and other body exudates. The liner 25 may be selectively embossed or perforated with discrete slits or holes extending therethrough. Optionally, the web or sheet may be treated with a surfactant to aid in liquid transfer. One preferred bodyside liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The shell 22 has a front waist section 27, an opposite back waist section 28, and a crotch area 29 (FIG. 1) which is generally located intermediate the front and back waist sections 27 and 28. The shell 22 also has a pair of side sections 30 and 31 laterally outward of the crotch area 29 and generally between the front and back waist sections 27 and 28. The crotch area 29 is preferably narrower than the front and back waist sections 27 and 28. The shape of the side sections 30 and 31 gives the shell 22 an hourglass or I shape and defines front ears 32a and 32b, which form part of the front waist section 27, and back ears 32c and 32d, which form part of the back waist section 28. Each of the front ears 32a and 32b and back ears 32c and 32d extend oppositely along the lateral cross-direction of the diaper 20. The front ears need not be the same size as the back ears.

In several locations, the disposable diaper 20 may include elastic members to conform the shape of the diaper to the wearer and minimize the potential for leakage. With additional reference to FIGS. 3 and 4, for example, the disposable diaper 20 includes elongated leg elastic members 33 positioned between the backing sheet 24 and the bodyside liner 25. The leg elastic members 33, which are located in the crotch area 29 and extend to the front and back waist sections 27 and 28, are spaced slightly inward from the edges of the side sections 30 and 31. The leg elastic members 33 may be substantially straight, as illustrated most clearly in FIG. 3, or may be partly or fully curved (not shown). Using ultrasonic bonds, adhesives or other suitable means, the leg elastic members 33 are attached to the backing sheet 24, the bodyside liner 25, or preferably both, in an extended condition. The leg elastic members 33 function to draw the side sections 30 and 31 of the diaper 20 to the legs of the wearer and form a seal therewith.

One preferred material for the leg elastic member 33 is a dry-spun coalesced multifilament elastomeric thread sold under the tradename LYCRA and available from I.E. Du Pont de Nemours and Company. Alternately, the leg elastic members 33 may be formed of other typical elastics utilized in the diaper-making art, such as a thin ribbon of natural rubber. Elasticity could also be imparted to the side sections by extruding a hot melt elastomeric adhesive between the backing sheet 24 and the bodyside liner 25. Other suitable gathering means for the side sections 30 and 31 of the diaper 20 are disclosed in U.S. Pat. Nos. 4,938,754 to Mesek and 4,388,075 to Mesek et al.

The disposable diaper 20 may also include waist elastic members 34 (FIGS. 3 and 5) in the front and back waist sections 27 and 28 of the shell 22. The waist elastic members 34 extend longitudinally in a transverse or lateral direction relative to the longitudinal axis of the diaper 20. The elastic members 34 are positioned generally between the ears 32 of the front and back waist sections 27 and 28. Most preferably, the waist elastic members 34 are positioned between the backing sheet 24 and the bodyside liner 25 and secured in an extended condition to both the backing sheet and the bodyside liner, using ultrasonic bonds, adhesives or other suitable means.

The waist elastic member 34 may be formed of the same materials as the leg elastic members 33. One particularly preferred waist elastic member 34, which is produced by the methods and apparatus disclosed in U.S. Pat. No. 4,657,802 to Morman and incorporated herein by reference, is a stretch-bonded nonwoven laminate containing a spunbond polypropylene outer facing that is bonded to an elastic meltblown core. Alternate materials useful for the waist elastic members 34 are disclosed in U.S. Pat. Nos. 4,861,652 and 4,916,005 to Lippert et al.

To enhance the containment and absorption of urine and other body exudates, the disposable diaper 20 preferably includes a pair of containment flaps 36 and 37. The flaps 36 and 37 extend longitudinally between the front and back waist sections 27 and 28 of the shell 22. The flaps 36 and 37 are positioned slightly inboard or inward of the edges of the respective side sections 30 and 31 and leg elastic members 33. Containment flaps as incorporated in the absorbent articles of the present invention are disclosed in U.S. Pat. Nos. 4,704,116 and 4,846,823 to Enloe, which are incorporated herein by reference to the extent that they are consistent herewith.

The containment flaps 36 and 37 can be attached to or formed from the bodyside liner 25. If the containment flaps 36 and 37 are attached to the bodyside liner 25, the flaps 36 and 37 may be formed of a material that is different than the material used for the bodyside liner. The material for the containment flaps 36 and 37 may be substantially liquid pervious or impervious. One particularly preferred material for the containment flaps 36 and 37 is a wettable polypropylene spunbond having a basis weight of 0.8 ounces per square yard and being random laid and bonded in a cross-hatched formation.

As illustrated best in FIG. 4, each containment flap 36 and 37 may be formed as a folded, elongated strip of material. The folded edges of the strip of material form a base 38, which may be sealed to the bodyside liner 25 using a continuous ultrasonic bond, a continuous strip of adhesive, a series of spotbonds, or other suitable means.

Each containment flap 36 and 37 includes a pair of elastic members 40 that are positioned within the folds of the containment flap material, remote from the base 38 of the flap. As shown in FIG. 4, the elastic members 40 are individual strands of elastic material. The illustrated embodiment includes two elastic members 40 for each containment flap, although the particular number of strands employed for each containment flap, and the type of elastic material, may vary. Each elastic member 40, for instance, may be a thin ribbon of elastic material or several strands of elastic string. Most preferably, each elastic member 40 is a dry-spun, coalesced multifilament elastomeric thread sold under the tradename LYCRA and available from I. E. Du Pont de Nemours and Company.

The longitudinal ends 41 (FIG. 3) of each containment flap 36 and 37 are located at the longitudinal ends of the diaper 20, at the front and back waist sections 27 and 28. The ends 41 of the containment flaps 36 and 37 are preferably laid down on the bodyside liner 25, with the elastic members 40 positioned inboard or inward of the bases 38. The ends 41 of the containment flaps 36 and 37 are then bonded to the bodyside liner 25 by ultrasonic bonds, adhesives or other suitable means, causing the containment flaps to bow slightly upward and inward (see FIGS. 1, 2, and 4) toward the crotch area 29 of the diaper. The containment flaps 36 and 37 tend to contain solid fecal material and increase resistance to leakage of urine and fluidic fecal material. Optionally, the elastic members 40 could be attached directly to the bodyside liner 25 (not shown).

Figure 3:
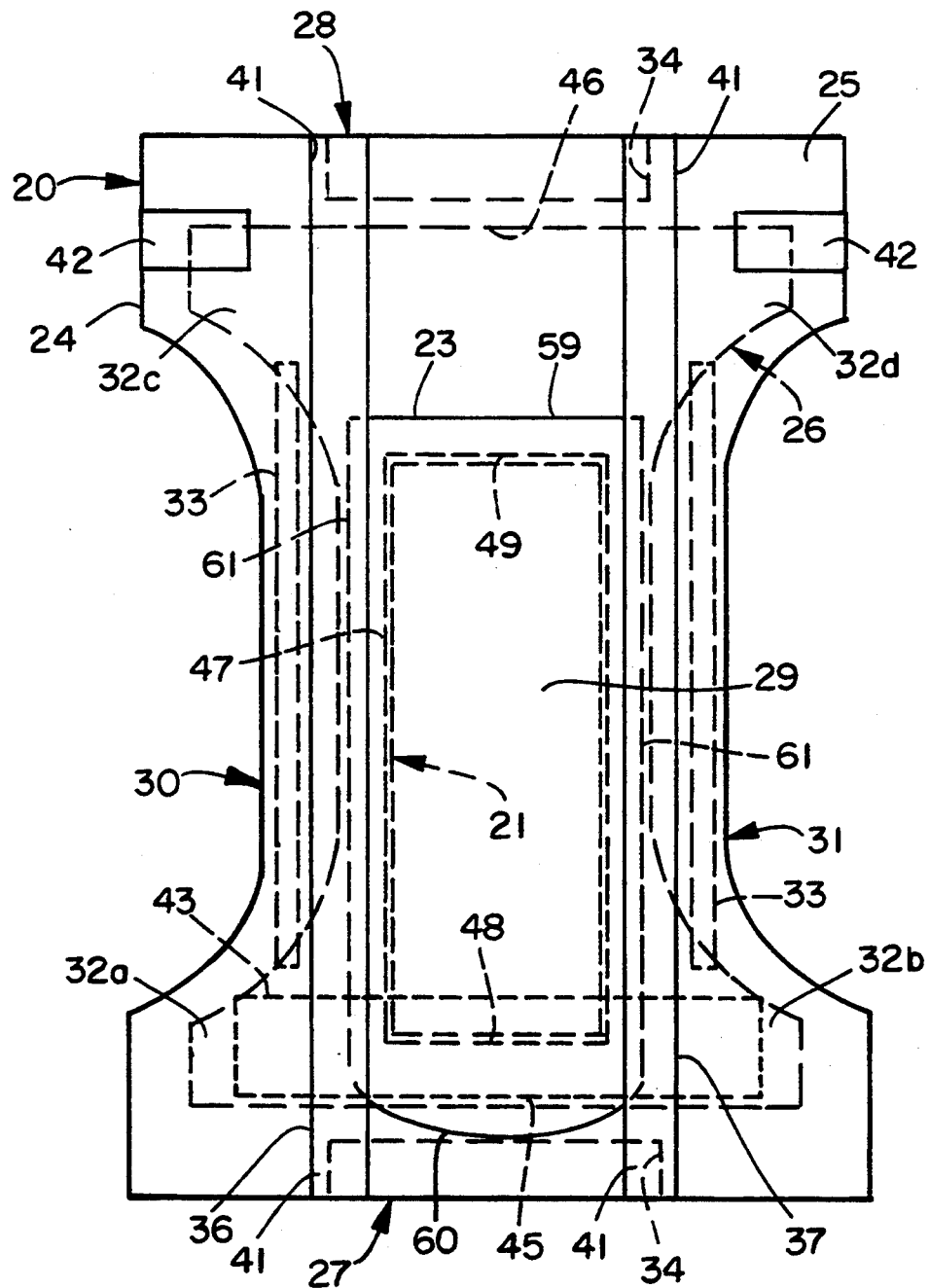
FIG. 3 is a top plan view of the absorbent article of FIG. 1, the absorbent article being in a stretched condition.

The diaper 20 is in its fully extended condition as shown in FIG. 3 only during the manufacturing process when a series of diapers are attached to each other in a continuous strip. When this continuous strip is cut to form individual diapers, the leg elastic members 33, the waist elastic members 34, and the containment flap elastic members 40 are substantially relieved of their tension and contract so that the diaper assumes a shape as illustrated in FIG. 1. The elastic members improve both the fit and the performance of the diaper 20.

Refastenable tape members 42 (FIGS. 1–3) are operably connected to the back ears 32c and 32d of the diaper 20. Each tape member 42 includes a fastening strip that may be releasably attached to a tape landing pad 43 (FIGS. 3 and 5). The landing pad 43 is fixed by adhesive or other suitable means to the surface of the backing sheet 24 that is remote from the bodyside liner 25. The tape members 42 and the landing pad 43 are positioned so that the fastening strips may be attached to the landing pad 43 when the diaper 20 is secured on a baby. The tape members 42 and the landing pad 43 may be formed of a polypropylene film and may be constructed in a manner as disclosed in U.S. Pat. No. 4,753,649 to Pazdernik, which is incorporated herein by reference. Other suitable fastening devices, such as hooks, snaps, cohesive strips and the like, could be used in place of the tape members 42 and the landing pad 43.

The secondary absorbent layer 26 (see FIGS. 3–5) includes a secondary absorbent body 44, which is preferably an air-formed batt of cellulosic fibers (i.e., wood pulp fluff). One preferred type of wood pulp fluff, which is available under the trade designation CR2054 from Kimberly-Clark Corporation of Neenah, Wisconsin, is a bleached, highly absorbent sulphate wood pulp containing softwood fibers. Optionally, the secondary absorbent body 44 could comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

The secondary absorbent body 44 may also include compounds to increase the absorbency of the body, such as an effective amount of organic or inorganic high-absorbency materials. For example, the secondary absorbent body 44 can include 0–95 weight percent high-absorbency material, and preferably includes 0–20 weight percent high-absorbency materials. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxpropyl cellulose, polyvinyl morpholinone, polymers and copolymers of vinyl sulfonic acid, polyacrylates, polyacylamides, polyvinyl pyridine and the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, and Allied-Colloid. Typically, the high-absorbency material is capable of absorbing at least about 15 times its weight in water, and preferably is capable of absorbing more than about 25 times its weight in water.

The high-absorbency materials may also be biodegradable high-absorbency materials. For example, the materials may be based on potato starch or other degradable substances. Suitable biodegradable high-absorbency materials are identified as Foxorb HR and Foxorb 15 and are available from Avebe b.a. of Foxhol, Holland.

The high-absorbency material can be distributed or otherwise incorporated into the secondary absorbent body 44 employing various techniques. For example, the high-absorbency material can be substantially uniformly distributed among the fibers comprising the absorbent body. The materials can also be nonuniformly distributed within the absorbent body fibers to form a generally continuous gradient with either an increasing or decreasing concentration of high-absorbency material, as determined by observing the concentration moving inward from the backing sheet 24. Alternatively, the high-absorbency material can comprise a discrete layer separate from the fibrous material of the secondary absorbent body 44, or can comprise a discrete layer integral with the absorbent body 44.

The periphery of the secondary absorbent body 44 is preferably although not necessarily formed in an hourglass or I shape similar to the shape of the backing sheet 24 and the bodyside liner 25. The overall size of the secondary absorbent body 44 is smaller than the backing sheet 24 and the bodyside liner 25, so that the backing sheet and the bodyside liner extend past the secondary absorbent body. Along their peripheries, the backing sheet 24 and bodyside liner 25 are bonded together using adhesives, ultrasonic bonds or other suitable means. The secondary absorbent body 44 is formed with a front section 45 and an opposite back section 46 (FIGS. 3 and 5). The secondary body 44 is positioned in the shell 22 so that the front section 45 is in the front waist section 27 of the shell 22 and the back section 46 is in the back waist section 28 of the shell.

Between its front and back sections 45 and 46, the secondary absorbent body 44 is formed with a pocket 47, that is preferably although not necessarily rectangular in shape. The pocket 47 is a central opening in the body 44, but may alternately be a region of the secondary absorbent body that has a lower basis weight, or is formed or compressed to be thinner, than the surrounding areas. If the pocket 47 is an opening in the secondary absorbent body 44, the opening may be formed in the fluff forming chamber, by die stamping, or other suitable means. The pocket 47 extends longitudinally toward the front and back sections 45 and 46 of the secondary absorbent body 44, and is centered between the sides of the body 44 and the side sections 30 and 31 of the diaper 20. Preferably, the pocket 47 is located in the region of the diaper 20 with the highest urine loading potential, which is slightly foreword of the longitudinal and transverse center of the diaper 20. Thus, the pocket 47 is preferably offset toward the front section 45 of the secondary absorbent body 44. A leading edge 48 of the pocket 47 is located slightly inward of the longitudinal end of the absorbent body 44 in the front section 45. An opposite trailing edge 49 of the pocket 47 is located generally intermediate the crotch area 29 and the longitudinal end of the absorbent body 44 in the back section 46 (see FIGS. 2, 3 and 5). In this way, the pocket 47 is positioned generally in the crotch area 29 and the area between the crotch 29 and the front waist section 27 of the diaper 20.

The secondary absorbent layer 26 also includes two wrapping sheets 50 (FIGS. 4 and 5) which cover the top and bottom surfaces of the secondary absorbent body 44 and extend into the pocket 47. The wrapping sheets 50 help maintain the integrity of the secondary absorbent pad 44 and contain the wood pulp fluff and any high-absorbency materials. The sheets 50 may for example comprise a wet-strength cellulosic material, such as a single-ply creped wadding.

The shown embodiment of the absorbent insert pad 21 is generally rectangular in shape and sized to reside within the pocket 47 (see FIGS. 4 and 5). The insert pad 21 includes an absorbent material 52, which may include wood pulp fluff and high-absorbency materials, as described previously. The insert pad 21 preferably although not necessarily includes less than about 80 weight percent of wood pulp fluff and at least about 20 weight percent of high-absorbency materials. Most preferably, the insert pad 21 contains less than about 50 weight percent of wood pulp fluff and at least about 50 weight percent of high-absorbency materials. Where high-absorbency materials are incorporated into the insert pad 21, the materials may be distributed or otherwise incorporated into the pad in a substantially uniform or a nonuniform distribution, employing a variety of techniques, as previously noted. The absorbent material 52 may for example have a density from about 0.05 to about 0.3 grams per cubic centimeter and a basis weight from about 50 to about 700 grams per square meter.

The absorbent material 52 is preferably wrapped in a flushable, dispersible carrier sheet 53. The carrier sheet 53 may comprise a low-wet-strength cellulosic tissue. Alternately, the carrier sheet 53 can comprise a nonwoven material such as a rayon carded web that is bonded with polyvinyl alcohol. One such material, is available under the trade designation PRK 20 from Bonded Fiber Fabrics of Bridgewater, Somerset, England. This material has been evaluated and found to have tensile strengths in the machine direction of approximately 7,650 grams (dry) and 371 grams (wet) and in the transverse direction of approximately 838 grams (dry) and 19 grams (wet).

The ends of the carrier sheet 53 may be folded onto themselves and bonded using sonic bonds, adhesives, or other suitable means to retain the absorbent material 52 within the carrier sheet. More preferably, the ends of the carrier sheet 53 are bonded with a time sensitive binder that will break down rapidly after being deposited in toilet bowl water. For example, the ends of the carrier sheet 53 may be bonded with a polyvinyl alcohol-based adhesive.

The longitudinally-extending sides of the carrier sheet 53 overlap slightly (see FIG. 4), and are preferably unbonded. These overlapping sides of the carrier sheet 53 allow absorbent material 52 to escape from within the carrier sheet once the insert pad 21 has been removed from the shell 22 and deposited in a toilet. Optionally, the carrier sheet 53 could be formed with slits or other openings therein. As another option, the absorbent material 52 could be covered by upper and lower carrier sheets (not shown) that are sealed along their ends, sides, or both. Still optionally, a lower carrier sheet (not shown) could cover one surface of the absorbent material and an upper carrier sheet (not shown) could cover the opposite surface, the ends, and the sides of the absorbent material. The periphery of the upper carrier sheet could overlap somewhat with the periphery of the lower sheet, where the peripheries of the two sheets could be bonded together. These optional designs for the carrier sheet 53 are advantageous in that the upper carrier sheet may be positioned toward the wearer and be formed of a material with a higher wet tensile strength than the lower carrier sheet. The upper sheet will thereby provide considerable durability during use while the lower sheet, formed with substantially no chemicals to add wet tensile strength, will disperse more readily when exposed to toilet bowl water.

The absorbent insert pad 21 is positioned against the bodyside liner 25 so as to be located generally within the pocket 47. Thus, at least a portion of the insert pad 21 is positioned in the space defined within the inside edges or walls of the secondary absorbent body 44, including the leading and trailing edges 48 and 49, that form the pocket. The whole insert pad 21 need not completely reside within the pocket 47. The insert pad 21 preferably although not necessarily has a thickness between about 0.06 inch and about 0.45 inch. The overlapping sides of the carrier sheet 53 are preferably positioned toward and adjacent the bodyside liner 25.

The cover 23 is used to retain the absorbent insert pad 21 within the pocket 47. The cover 23 comprises an upper insert liner 56 and a lower transfer layer 57 that are substantially coterminous and in facing relationship (see FIGS. 4 and 5). The insert liner 56 may be formed of the same material as the bodyside liner 25 and is preferably a substantially fluid pervious material such as an apertured, spunbonded polypropylene. The transfer layer 57 is formed of a material to provide adequate transfer of fluids and enhance diaper dryness, and may be formed as disclosed in U.S. Pat. No. 4,798,603, to Meyer et al. which is incorporated herein by reference to the extent that it is consistent herewith. Preferably, the transfer layer 57 comprises a wettable spunbonded material formed of continuous polypropylene filaments and having a basis weight of 1.0 ounce per square yard. The insert liner 56 and the transfer layer 57 are bonded together, preferably along their perimeters using ultrasonic bonds, adhesives or other suitable means. Optionally, the cover 23 could be formed of only a single layer of material, or formed of a flushable material and discarded into the toilet along with the insert pad 21.

The cover 23 is generally although not necessarily rectangular in shape and, as shown best in FIG. 3, is somewhat longer and wider than the dimensions of the pocket 47. The cover 23 has a recessed edge 59, an opposite exposed edge 60, and longitudinal sides 61 extending between the recessed and the exposed edges 59 and 60. As shown in FIG. 5, the recessed edge 59 is positioned rearward of the trailing edge 49 of the pocket 47, and the exposed edge 60 is positioned forward of the leading edge 48 of the pocket. Both the recessed edge 59 and the exposed edge 60 are positioned above the secondary absorbent body 44. As shown in FIG. 4, the sides 61 of the cover 23 are positioned outward of the pocket 47, over the secondary absorbent body 44. The width of the cover 23 is preferably such that the cover fits between the base portions 38 of the containment flaps 36 and 37. Optionally, the containment flaps 36 and 37 could be partially or completely attached to the cover 23 inboard of the sides 61, rather than being attached to the bodyside liner 25.

The periphery of the cover 23 is releasably attached to the diaper 20 by peelable bonds 63 (FIGS. 4 and 5) that join the transfer layer 57 and the bodyside liner 25. The bonds 63 are situated near the periphery of the cover 23 and above the secondary absorbent body 44. Thus, the peelable bonds 63 releasably attach the cover 23 to the liner 25 at a location immediately outward from and adjacent to the pocket 47. The peelable bonds 63 may be ultrasonic bonds, adhesive bonds, or other suitable releasable bonds.

The exposed edge 60 of the cover 23 is formed by the transfer layer 57, which extends a short distance past the front edge of the insert liner 56 (see FIG. 5). Alternately, the exposed edge 60 could be formed by a portion of the transfer layer 57 and the insert liner 56, or a portion of the insert liner alone. The peelable bonds 63 at the front of the cover 23 are located slightly inward of the exposed edge 60, so that the user may easily grasp the exposed edge to remove the cover. The exposed edge 60 is generally rounded (see FIGS. 1-3), and may optionally include a finger-sized aperture (not shown) to assist in removing the cover 23 from the remainder of the diaper 20.

In use, the disposable diaper 20 is secured to the baby using the tape members 42. The waist elastic members 34 and the leg elastic members 33 aid in fitting the particular diaper 20 to the individual baby. The waist elastic members 34, the leg elastic members 33, and the elasticized containment flaps 36 and 37 limit leakage by containing urine and fecal material.

With a diaper 20 constructed in accordance with the present invention, urine is principally absorbed by, and contained within, the absorbent insert pad 21. The urine initially contacts the cover 23 where it quickly passes through the upper insert liner 56 to the transfer layer 57. The transfer layer 57 functions to remove moisture from the insert liner 56 and promote movement of liquids into the absorbent insert pad 21. The urine passes substantially through the carrier sheet 53 and is absorbed by the absorbent material 52 of the insert pad 21. The containment flaps 36 and 37 increase the effectiveness of the insert pad 21 by retarding the lateral movement of urine and other fluidic material away from the insert pad. Thus, the insert pad 21 functions as the primary absorbent for the diaper 20.

In the case of a large insult, urine and other fluidic substances may pass through the bodyside liner 25 and into the secondary absorbent layer 26. In that case, liquid may pass substantially through the wrapping sheets 50 to be absorbed by the secondary absorbent body 44. The positioning of the absorbent insert pad 21 in the region of the diaper 20 with the highest urine loading potential, however, causes a majority of the urine to be absorbed by the insert pad.

The disposable diaper 20 is designed for single-use applications. The diaper 20 is also designed so that the absorbent insert pad 21 can be removed from the diaper after use and discarded into a toilet bowl. The absorbent insert pad 21 may be allowed to reside within the bowl water for a brief period to become substantially saturated or begin to disperse. The insert pad 21 may then simply and conveniently be flushed down any toilet that is connected to a holding tank, a municipal sewer, or other municipal wastewater treatment system. Where the insert pad 21 is formed of wood pulp fluff or biodegradable high-absorbency materials, the pad may also be flushed in toilets connected to other types of residential wastewater treatment systems.

Figure 6:
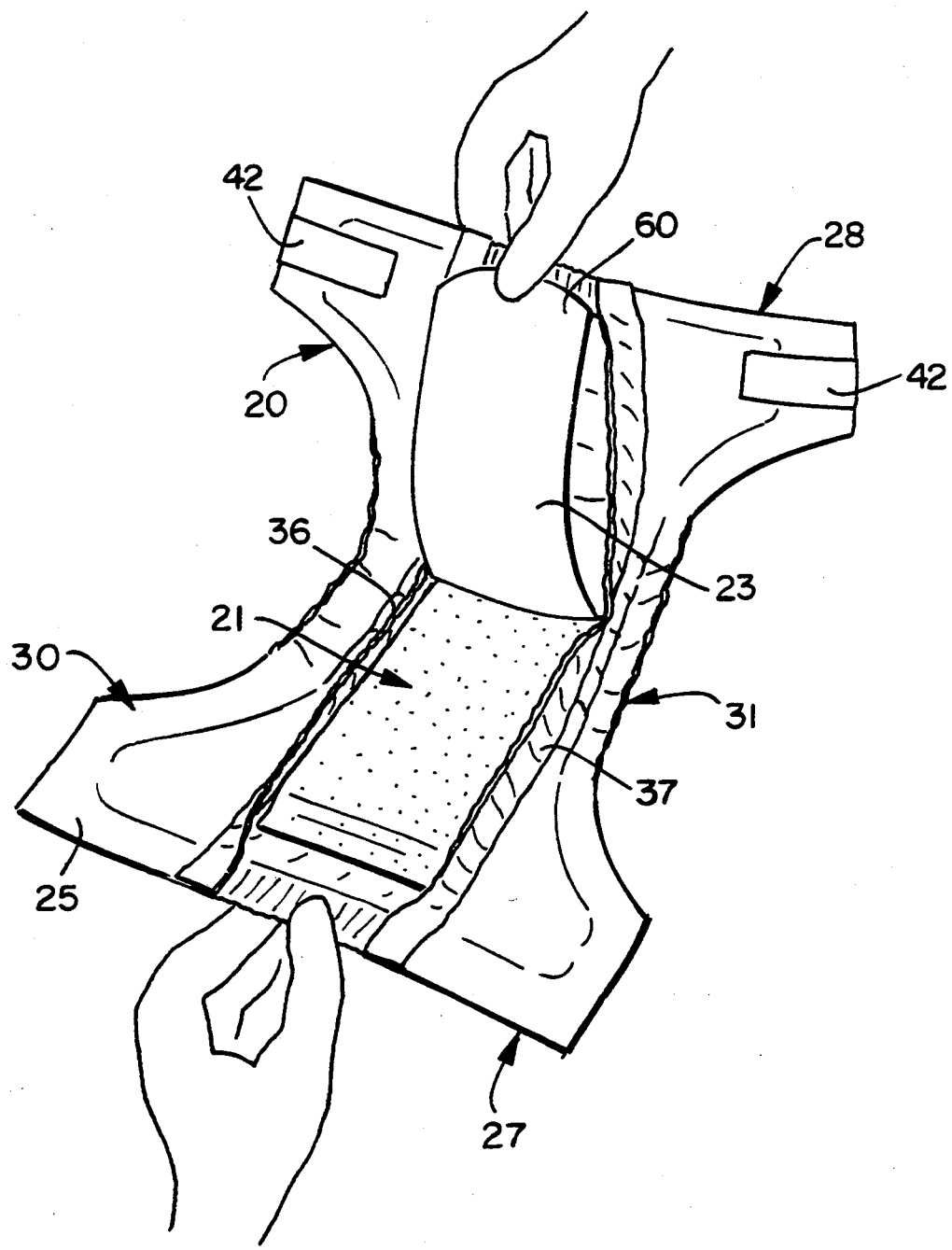
FIG. 6 is a perspective view illustrating an initial step in the disposal of an absorbent insert pad of the absorbent article of FIG. 1.
Figure 7:
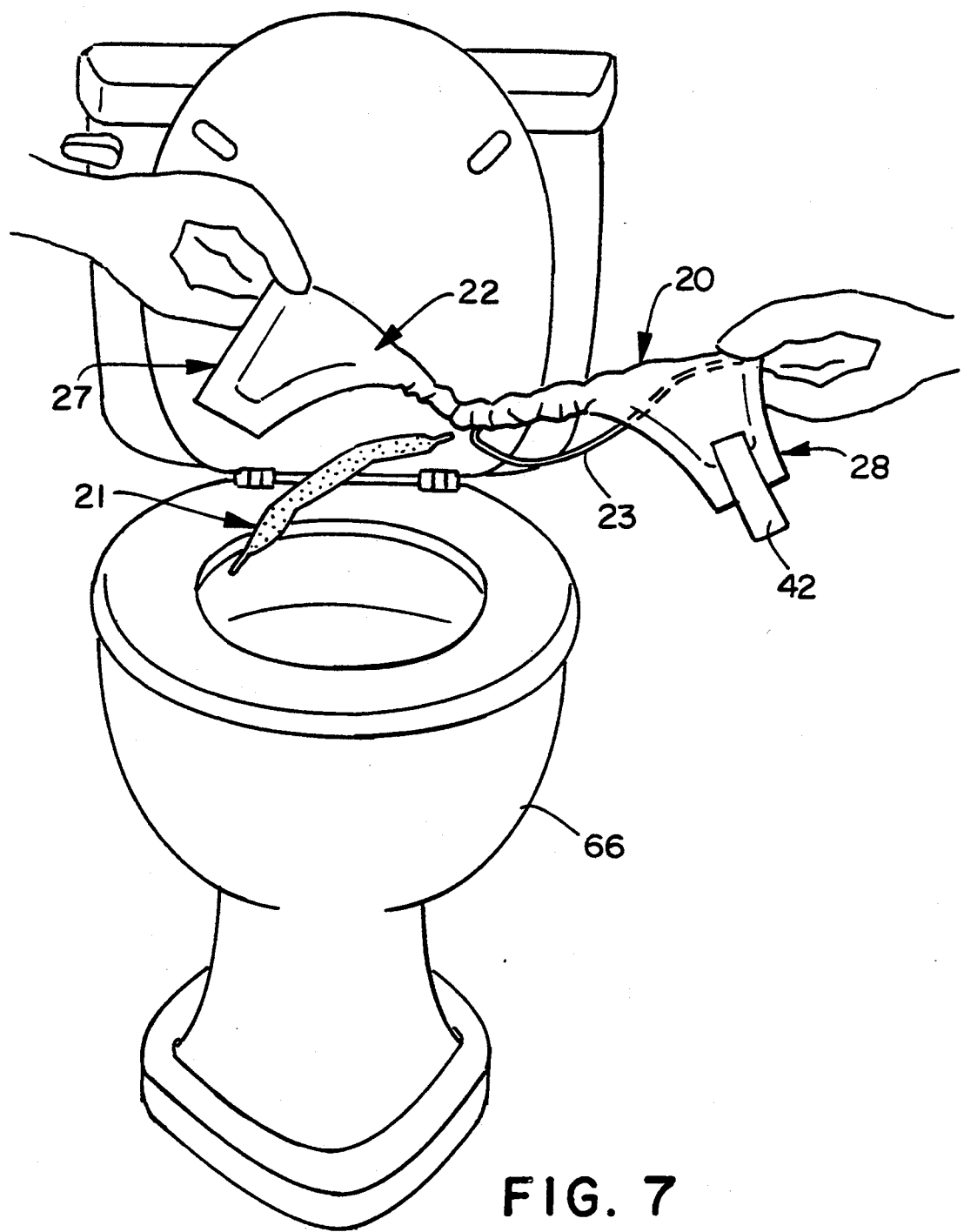
FIG. 7 is a perspective view illustrating a further step in the disposal of the absorbent insert pad of the absorbent article of FIG. 1.

One method of removing the absorbent insert pad 21 after use is illustrated in FIGS. 6 and 7. With the diaper 20 in a folded position such that the front waist section 27 is positioned near the back waist section 28 (not shown), the parent grasps the front waist section 27 with one hand and grasps the back waist section 28 and the exposed edge 60 of the cover 23 with the other hand. The parent then pulls the front waist section 27 away from the back waist section 28 and the exposed edge 60, thereby breaking the peelable bonds 63 and exposing the absorbent insert pad 21 (see FIG. 6). When the cover 23 has been pulled back a sufficient distance to expose a majority of the pocket 47 and the insert pad 21, the diaper 20 may be inverted to allow the absorbent insert pad 21 to fall by gravity into a toilet 66 (see FIG. 7).

As will be appreciated, a diaper 20 embodying the present invention provides for extremely easy removal of the flushable insert pad 21. The parent need not contact the absorbent insert pad 21 directly, and thus the parent's hands do not become soiled when disposing of the insert pad 21. The shell 22 and the cover 23, which remain after removing the absorbent insert pad 21, may be stored for subsequent transport to a solid waste disposal site. Optionally, where appropriate facilities are available, the shell 22 and cover 23 may be recycled or composted.

Upon contacting the water in the toilet, the components of the absorbent insert pad 21 begin to disperse. Additionally, where the binder used to seal the ends of the carrier sheet 53 comprises a binder that will rapidly break down in the presence of toilet bowl water, the carrier sheet tends to open at its ends. This may then cause the overlapping, unbonded sides of the carrier sheet 53 to separate. Further, the wood pulp fluff and the high-absorbency materials of the absorbent material 52 may absorb bowl water. The carrier sheet 53 and absorbent material 52 may be flushed down the toilet. The insert pad 21 may also be allowed to reside in the bowl water prior to flushing, preferably less than two minutes.

Several other options are available to a parent using the disclosed diaper. For example, the parent can easily deposit solid fecal waste from the diaper 20 into the toilet, given that the parent is positioned near the toilet to dispose of the absorbent insert pad 21. Another option is for the parent to completely remove the non-flushable cover 23 from the shell 22. The feces adhered to the cover 23 may be rinsed in the toilet bowl to more completely dispose of such material in the toilet. Optionally, any dry portion of the cover 23 could be used to wipe the child's bottom, prior to rinsing the cover. In all of these scenarios, solid feces material may be removed from the diaper for flushing without any need for the parent to touch the feces or the absorbent insert pad 21.

The hydraulic action of flushing the insert pad 21 and transporting it to a municipal wastewater treatment facility will further break down the absorbent material 52 and carrier sheet 53 of the insert pad 21 into individual particles and fibers that can be accommodated by the municipal facility. The low-wet strength carrier sheet 53 has been found to completely break apart after several hours in a water stream. The insert pad 21 can also be flushed into a holding tank system or, where the absorbent material 52 is wood pulp fluff and biodegradable high-absorbency materials, into other types of residential systems.

The disposable diaper 20 of the present invention provides a significant advantage over prior diapers which were completely sent to solid waste refuse sites. Flushing the absorbent insert pad 21 and the feces material down the toilet reduces by about one-half the weight amount that would normally have to be sent to a solid waste disposal facility using a completely non-flushable diaper. Furthermore, the components of the diaper that are not flushed down the toilet, such as the backing sheet 24, bodyside liner 25, secondary absorbent body 44, cover 23, containment flaps 36 and 37, elastic members 33, 34, and 40, and the tape members 42, may be recycled or composted if such facilities are locally available.

Figure 8:
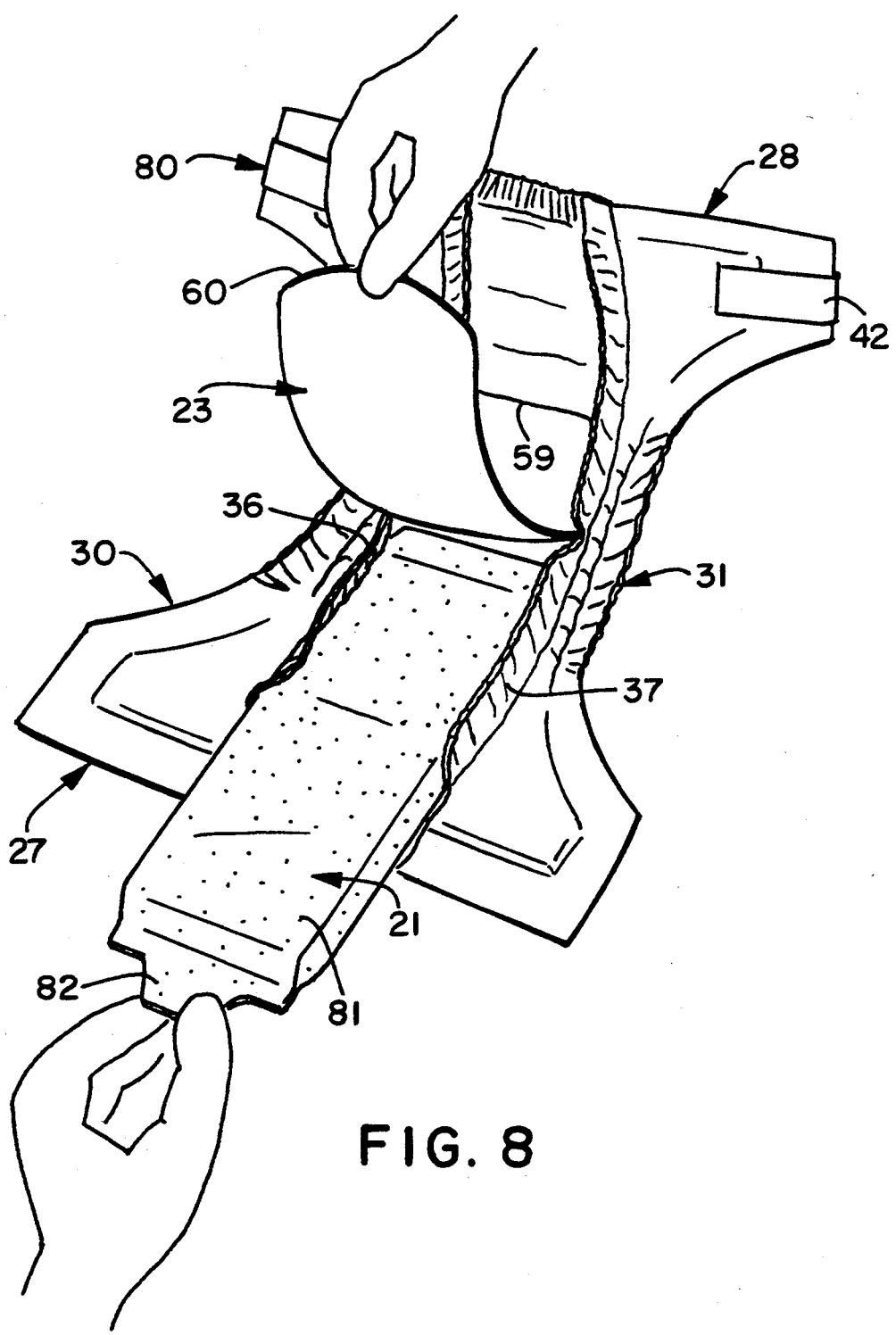
FIG. 8 is a perspective view illustrating disposal of an absorbent insert pad of a second embodiment of the present invention.

A second embodiment of the present invention is illustrated by diaper 80 in FIG. 8, where components similar to those previously described have the same reference numeral. The flushable absorbent insert pad 21 in this embodiment employs a carrier sheet 81 that is formed at one end of the pad with a tab 82. When the insert pad 21 is positioned within the pocket 47 with the tab 82 toward the front waist section 27, the tab resides on the bodyside liner 25 at a location above the front section 45 of the secondary absorbent body 44. The tab 82 projects from the pocket 47 and is positioned generally beneath the exposed edge 60 of the cover 23. Optionally, the tab 82 could project past the exposed edge 60. The recessed edge 59 and the sides 61 of the cover 23 are releasably secured to the bodyside liner 25, while the exposed edge 60 is preferably not secured to either the bodyside liner 25 or the carrier sheet 81. Alternately, the exposed edge 60 may be lightly, releasably bonded to the bodyside liner 25 using sonic bonds, adhesives, or other suitable means.

To remove the flushable insert pad 21 from this diaper 80, the parent pulls the exposed edge 60 of the cover 23 away from the front waist section 27 to break the peelable bonds 63 and expose a majority of the insert pad. In doing so, the tab 82 of the carrier sheet 81 is exposed to view. The parent may then grasp the tab 82 and pull the absorbent insert pad 21 from the pocket 47. To assist in removing the insert pad 21, the tab could optionally be formed with a finger-sized aperture (not shown). After removing the insert pad 21 from the pocket 47, the insert pad may then be placed in a toilet bowl and subsequently flushed, as previously described. Additionally, the parent may deposit any solid fecal material in the toilet, and remove and rinse the cover 23 in the toilet. The tab 82 provides a convenient means for the parent to control the position of the insert pad 21 prior to flushing, while still minimizing the parent's exposure to bodily waste.

Figure 9:
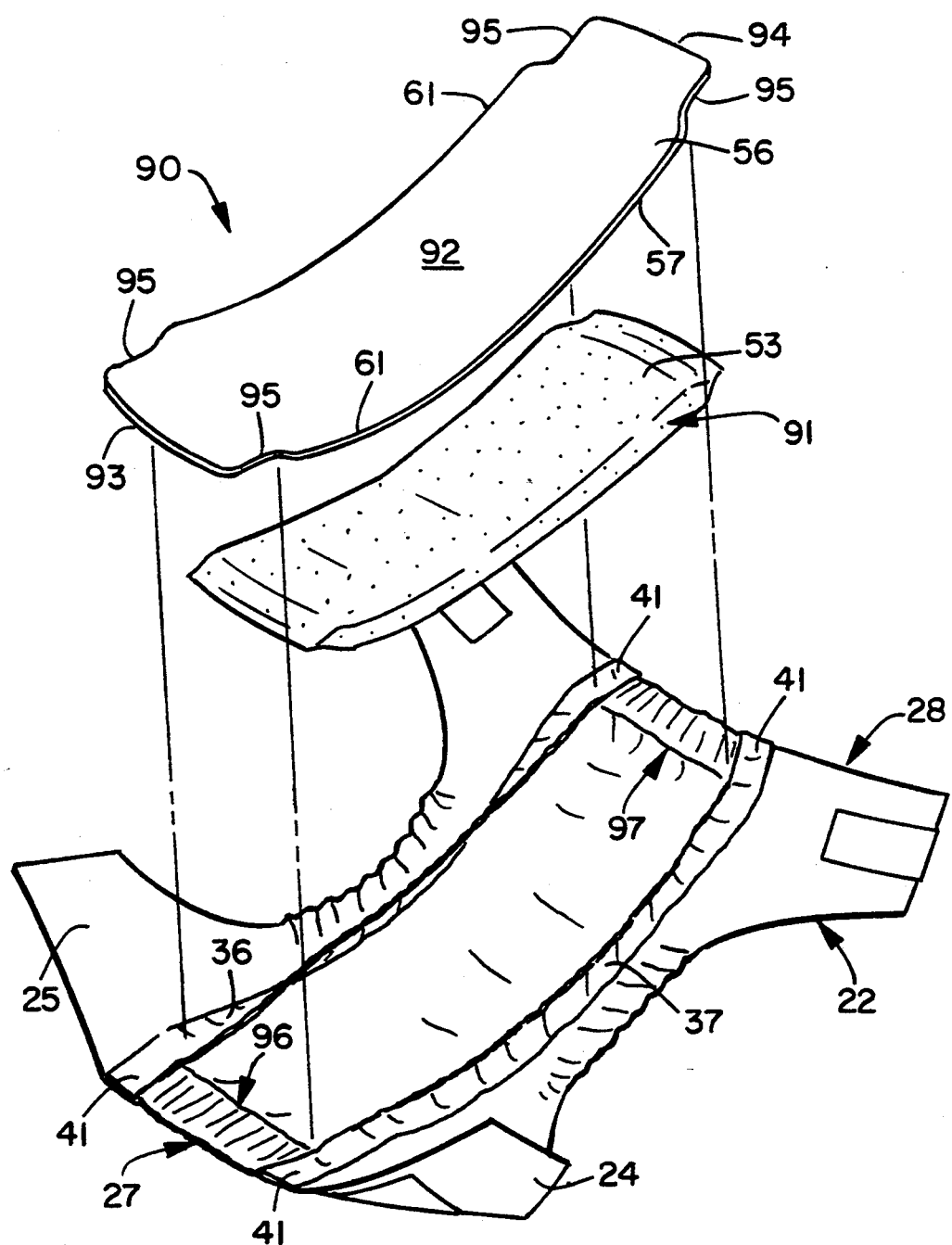
FIG. 9 is an exploded perspective view of a third embodiment of an absorbent article according to the present invention.
Figure 10:
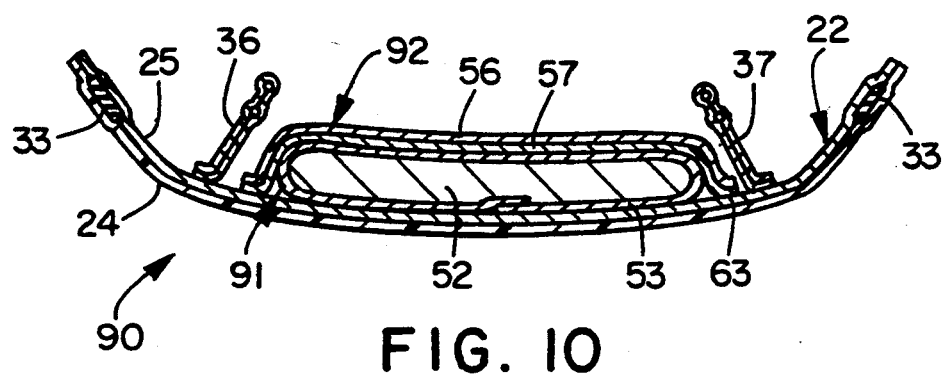
FIG. 10 is an enlarged view in section, similar to FIG. 4, but relating to the absorbent article of FIG. 9.

A third embodiment of the invention is illustrated by the diaper 90 shown in FIGS. 9 and 10. In this embodiment, the diaper 90 comprises a shell 22 that includes a bodyside liner 25 and a backing sheet 24, but does not include a secondary absorbent layer (such as layer 26 in FIGS. 3–5) between the bodyside liner and the backing sheet. The bodyside liner 25 is secured directly to the backing sheet 24, in face-to-face, intimate contact, using adhesives or other suitable means.

The diaper 90 of FIGS. 9 and 10 further includes leg elastic members 33, waist elastic members 34, and elasticized containment flaps 36 and 37 to contain urine and fecal material. An absorbent insert pad 91 of the diaper 90 is formed of an absorbent material 52 that is wrapped in a carrier sheet 53. The width of the absorbent insert pad 91 is appropriate to fit between the containment flaps 36 and 37, and the length of the pad is appropriate to fit generally between the front and back waist elastic members 34, such as to the longitudinal end areas, designated by arrows 96 and 97 in FIG. 9.

The absorbent insert pad 91 is releasably retained against the bodyside liner 25 by a cover 92 that comprises an upper insert liner 56 and a lower transfer layer 57. Optionally, the cover 92 could comprise a single layer or have an upper transfer layer and a lower insert liner. The cover 92 has an exposed front edge 93 and an opposite exposed back edge 94, with sides 61 extending between the exposed front and back exposed edges. The corners 95 between the sides 61 and the front and back exposed edges 93 and 94 are recessed. The cover 92 is sized so that the exposed front edge 93 lies adjacent the front waist section 27 near the front waist elastic member 34, and the exposed back edge 94 lies adjacent the back waist section 28 near the back waist elastic member 34.

The sides 61 of the cover 92 extend over the longitudinal sides of the absorbent insert pad 91, and are releasably secured to the bodyside liner 25 by peelable bonds 63. The sides 61 of the cover 92 are located inward of the containment flaps 36 and 37. The recessed corners 95 cause the cover 92 to avoid the containment flap ends 41, which are folded toward the central, longitudinal axis of the diaper and secured to the bodyside liner 25. As an alternative (not shown), the containment flaps 36 and 37 could be formed from, or attached to, the periphery of the cover 92, rather than being formed from, or attached to, the bodyside liner 25.

Compared to the embodiments depicted in FIGS. 1–8 which may be said to utilize a partial-length flushable insert, the diaper 90 of FIGS. 9 and 10 provides a full-length, flushable absorbent insert pad 91. The partial-length insert pad may have a length dimension between about 8 and about 10½ inches, for example, while the full-length insert pad may have a length dimension between about 10½ and about 15 inches, for example. Both the partial-length and the full-length pads may preferably have a width dimension between about 2 and about 4½ inches. Additionally, because this embodiment does not employ a secondary absorbent layer, all of the absorbent material 52 of the diaper is contained in the absorbent insert pad 91. Thus, all of the absorbent material 52 of this diaper 90 can be emptied into and subsequently flushed down a toilet.

To dispose of the full-length insert pad 91, the cover 92 is at least partially separated from the diaper shell 22 by pulling on either the exposed front edge 93 or the exposed back edge 94 to break the peelable bonds 63. The parent thus has the option of touching either the front edge 93 or the back edge 94, whichever is drier or more convenient. After removing the cover 92 a distance sufficient to expose a majority of the insert pad 91, the diaper 90 may be inverted to allow the absorbent insert pad 91 to fall by gravity into a toilet. The absorbent insert pad 91 may then be flushed, or may be allowed to reside in the bowl water prior to flushing, preferably less than two minutes.

The larger absorbent insert pad 91 of this embodiment enables a greater percentage by weight of the diaper to be disposed of by flushing rather than delivery to a solid waste disposal facility. In fact, flushing the full-length absorbent insert pad 91 and the feces material down the toilet reduces by substantially more than half the weight amount that would normally have to be sent to a solid waste disposal facility using a completely non-flushable diaper. Additionally, the cover 92 may be fully separated from the bodyside liner 25 and rinsed in the toilet bowl to more completely dispose of any solid fecal material.

Figure 11:
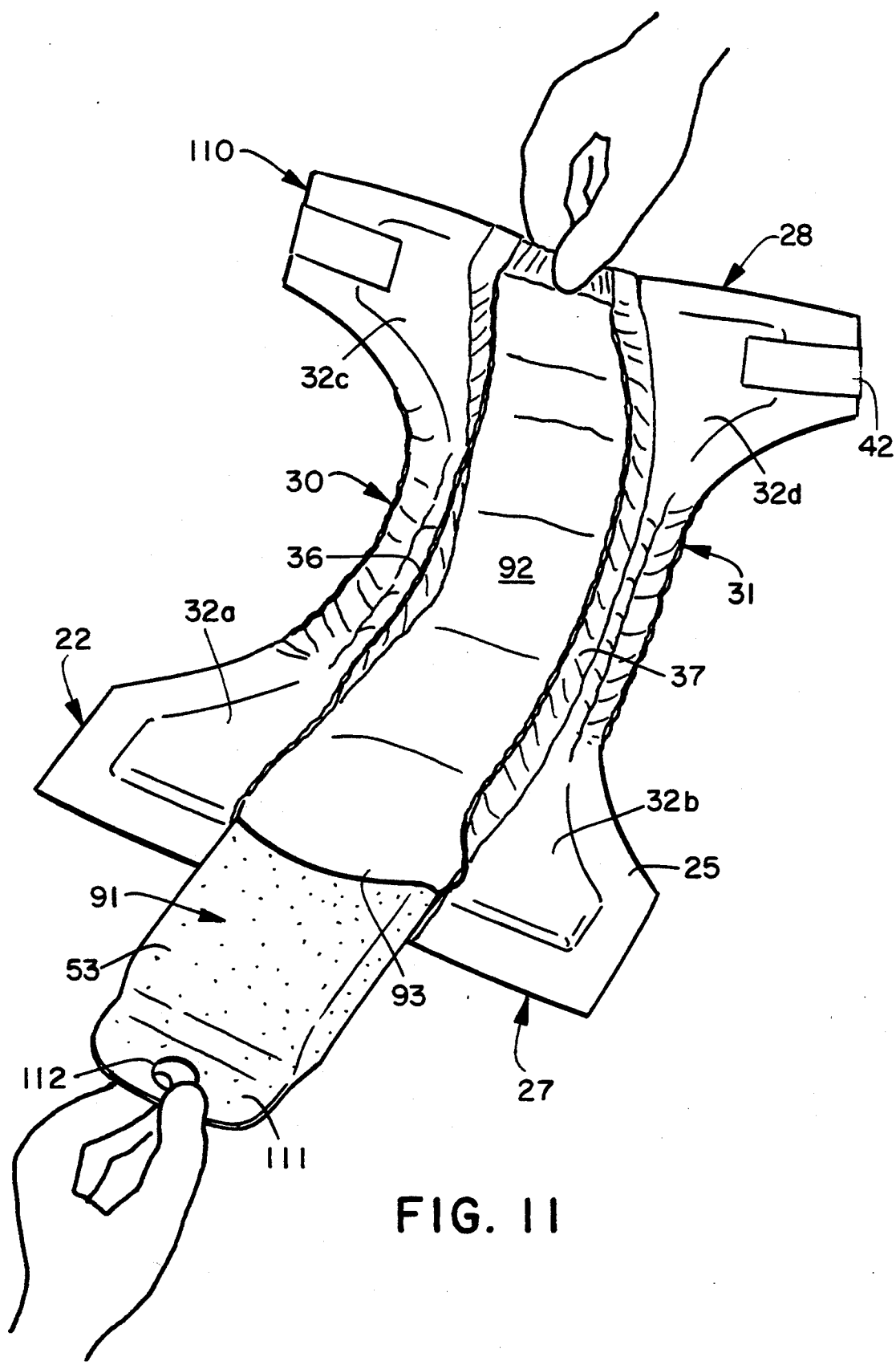
FIG. 11 is a perspective view illustrating disposal of an absorbent insert pad of a fourth embodiment of the present invention.

A fourth embodiment of the present invention is illustrated by the diaper 110 of FIG. 11. A shell 22 of the diaper includes a secondary absorbent body 44 having a pocket 47 that extends substantially the full-length of the diaper. A flushable, absorbent insert pad 91 of the diaper is sized to reside within the pocket 47. The insert pad 91 comprises a carrier sheet 53 that contains an absorbent material 52. The carrier sheet 53 is formed with a rounded end 111 that is located adjacent the front waist section 27, but alternately could be located near the back waist section 28. The rounded end 111 includes a finger-sized aperture 112 therethrough.

The full-length absorbent insert pad 91 is retained within the pocket 47 (not shown in FIG. 11) by a cover 92. The longitudinally-extending sides 61 of the cover 92 are positioned outboard or outward of the pocket 47 and between the base portions 38 of the containment flaps 36 and 37. Optionally, the containment flaps 36 and 37 could be formed on the cover 92. The sides 61 are releasably attached to the bodyside liner 25 by peelable bonds 63. The rounded end 111 of the carrier sheet 53 protrudes from beneath an exposed front edge 93 of the cover 92. Optionally, the rounded end 111 may be located beneath the exposed front edge 93 so that it becomes visible only upon lifting the front edge.

Once the diaper 110 has been soiled, the absorbent insert pad 91 may be removed from the pocket 77 for disposal into a toilet. This may be accomplished by pulling on the rounded end 111, using the aperture 112 if desired, while holding the opposite waist section of the diaper, as suggested by FIG. 11. The carrier sheet 53 may be reinforced with additional layers of a flushable, dispersible material at the rounded end 111 to provide added strength for pulling the insert pad 91 from the pocket 77. Preferably, the carrier sheet 53 has a wet tensile strength in the machine direction between about 100 grams and about 1,000 grams, and more preferably between about 300 grams and about 500 grams. This diaper 110 allows the parent to control the position of the insert pad 91 prior to placing the insert pad 91 in the toilet, while still minimizing the parent's contact with soiled portions of the diaper. As with other embodiments, the cover 92 may conveniently be removed from the shell 22 for rinsing in the toilet bowl.

Figure 12:
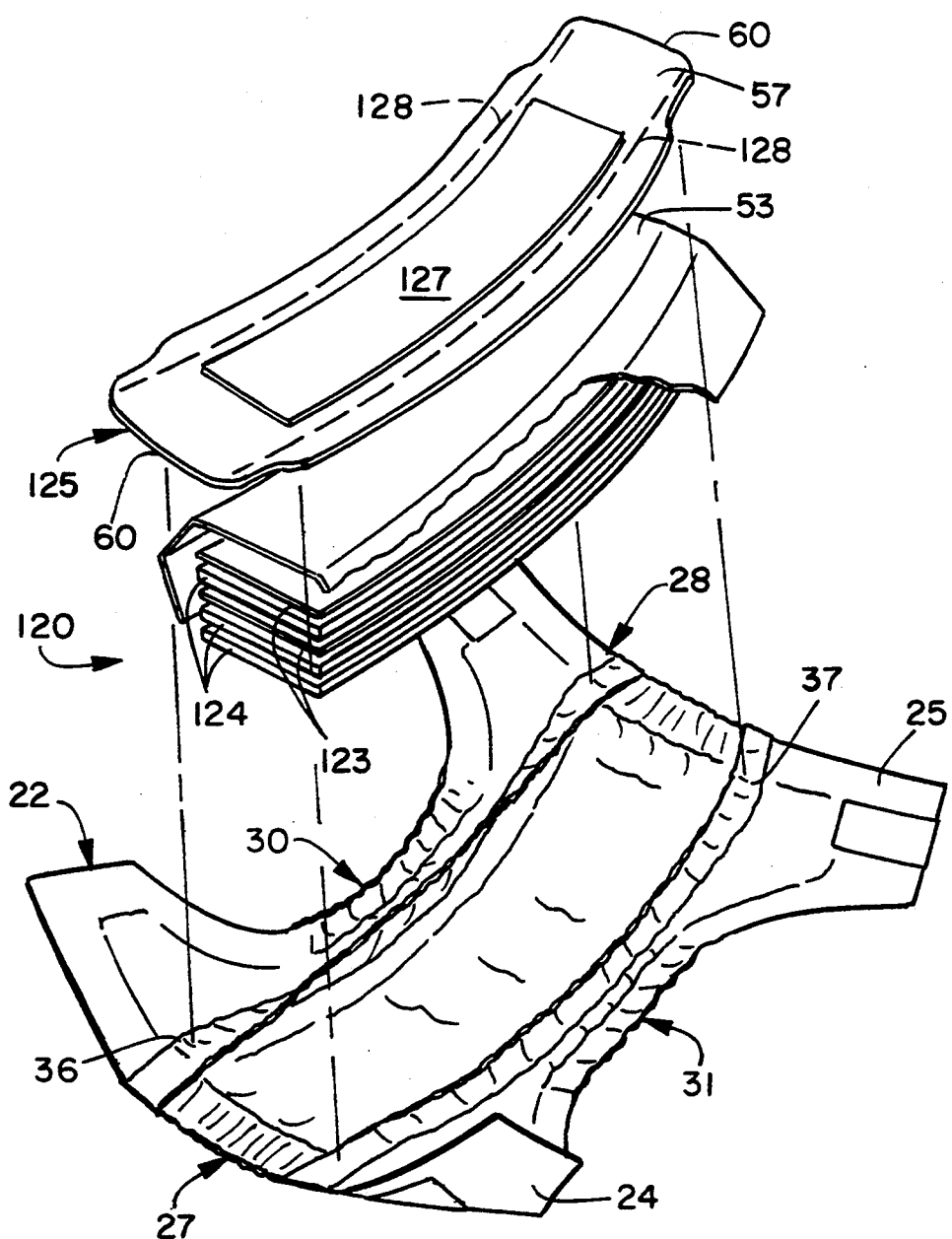
FIG. 12 is an exploded perspective view of a fifth embodiment of an absorbent article according to the present invention, with portions broken away for the purposes of illustration.
Figure 13:
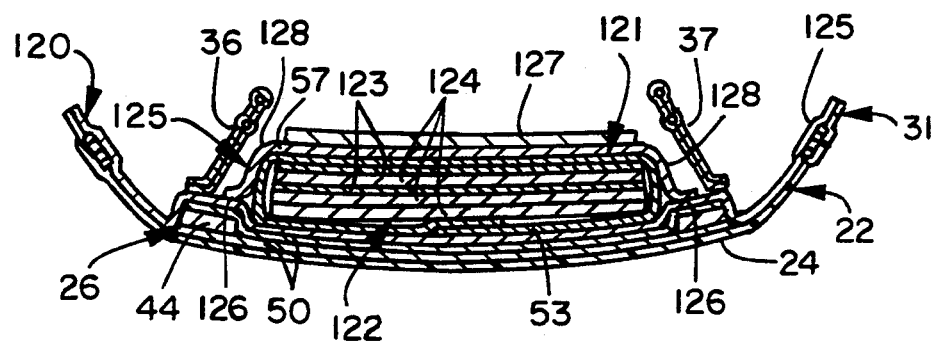
FIG. 13 is an enlarged view in section, similar to FIG. 4, but relating to the absorbent article of FIG. 12, with several components disproportionately enlarged for the purposes of illustration.

A fifth embodiment of the invention is illustrated by an especially thin diaper 120 illustrated in FIGS. 12 and 13, shown not to scale for purposes of clarity. The diaper comprises a shell 22 having a backing sheet 24, a bodyside liner 25, and a secondary absorbent layer 26 therebetween. The secondary absorbent layer 26 (FIG. 13) includes a relatively thin secondary absorbent body 44 that is covered on its top and bottom faces by wrapping sheets 50. The secondary absorbent body 44 preferably comprises two elongated, C-shaped portions. The C-shaped portions are located on opposite sides of the diaper 120 and are positioned in the ears 32 and side sections 30 and 31. The secondary absorbent body 44 is preferably formed principally of wood pulp fluff, but may also comprise coform material or high-absorbency materials.

A thin full-length, flushable absorbent insert pad 121 of the diaper 120 is sized to reside between the containment flaps 36 and 37 and generally between the front and back waist elastic members 34 (not shown). The insert pad 121 comprises a carrier sheet 53 that is wrapped about an absorbent material 122. The absorbent material 122 comprises two low-wet-strength cellulosic tissue sheets 123 and three thin absorbent sheets 124. The sheets 123 and 124 are arranged with a tissue sheet 123 on the top (away from the shell 22), then a thin absorbent sheet 124, then another tissue sheet, followed by two thin absorbent sheets positioned above and located toward the bodyside liner 25. The exact number and arrangement of sheets may be varied. The tissue sheets 123 function to distribute fluids and maintain the integrity of the thin absorbent sheet 124. The overall thickness of the insert pad 121 is preferably between about 0.06 inch to about 0.45 inch. For purposes of illustration, the components of the insert pad 121 have been disproportionately enlarged in thickness in the Figures.

The thin absorbent sheets 124 comprise high-absorbency materials and natural or synthetic fibers, such as polymeric, rayon or wood pulp fibers. The amount of high-absorbency materials in a sheet 124 is preferably between about 20 and about 90 weight percent, and more preferably between about 50 and about 85 weight percent. One suitable thin absorbent sheet is a wet-formed composite structure comprising a combination of high-absorbency materials and natural or synthetic fibers. The composite structure and its method of manufacture are described in a U.S. patent application Ser. No. 744,137, by Anderson et al., titled "Wet-Formed Absorbent Composite", which was filed on Aug. 13, 1991 and assigned to the assignee of the present invention, and which is incorporated herein by reference to the extent that it is consistent herewith. Another suitable thin absorbent sheet is a dry-formed composite structure comprising a combination of high-absorbency materials and natural or synthetic fibers. This composite structure and its method of manufacture are described in U.S. patent application Ser. No. 805,126, by Veith et al., titled "High Absorbency Composite", which was filed on Dec. 11, 1991 and assigned to the assignee of the present invention, and which is incorporated herein by reference to the extent that it is consistent herewith.

The absorbent insert pad 121 of FIGS. 12 and 13 is releasably held in place against the bodyside liner 25 by a cover 125. The cover 125 includes an transfer layer 57 that is attached along its sides to the bodyside liner 25 by suitable bonds 126, which may be a continuous line or series of ultrasonic bonds, adhesive bonds or the like. The transfer layer 57 is formed with rounded corners and has exposed front and back edges 60 that are positioned adjacent the front and back waist elastic members 34 (not shown in FIGS. 12 and 13).

The cover 125 also includes a rectangular surge layer 127 attached to the top of the transfer layer 57 by ultrasonic bonds, adhesives, or other suitable means. The length and width of the surge layer 127 are approximately the same as the length and width of the absorbent insert pad 121, and the surge layer is positioned on the transfer layer 57 at a location that corresponds to the location of the insert pad. The surge layer 127 is formed of a material that is capable of rapidly absorbing multiple, large volume urine insults. One suitable material is a polyester powder bonded carded web available from Bonar Fabrics under the tradename PBCW 1021, which material has a basis weight of about 50 grams per square meter. Optionally, the surge layer 127 may be positioned beneath the transfer layer 57, or the cover 125 may be formed of a single liquid permeable material.

To facilitate removal of the absorbent insert pad 121, the transfer layer 57 has two predetermined longitudinally-extending lines of relative weakness, such as lines of perforations 128. The perforation lines 128 extend the complete length of the transfer layer 57. The lines 128 are oriented parallel to the sides of the surge layer 127, and are located between the adhesive bonds 126 (FIG. 13) and the longitudinal sides of the surge layer. Optionally, the lines of relative weakness could be areas of the transfer layer 57 that are weakened by ultrasonics or other suitable means.

The absorbent insert pad 121 can be removed from the shell 22 by pulling either the front or back exposed edge 60 of the cover 125 away from the shell. This causes the transfer layer 57 to tear along the perforation lines 128, thereby exposing the absorbent insert pad 121. When a majority of the transfer layer 57 has been torn, the diaper 120 may be inverted to allow the insert pad 121 to fall by gravity into a toilet. The cover 125, including the surge layer 127 and the portion of the transfer layer 57 between the perforation lines 128, may be fully removed from the shell 22 so that it can be rinsed in the toilet. The insert pad 121 may then be flushed in the toilet, or may be allowed to reside in the bowl water prior to flushing, preferably less than two minutes.

Figure 14:
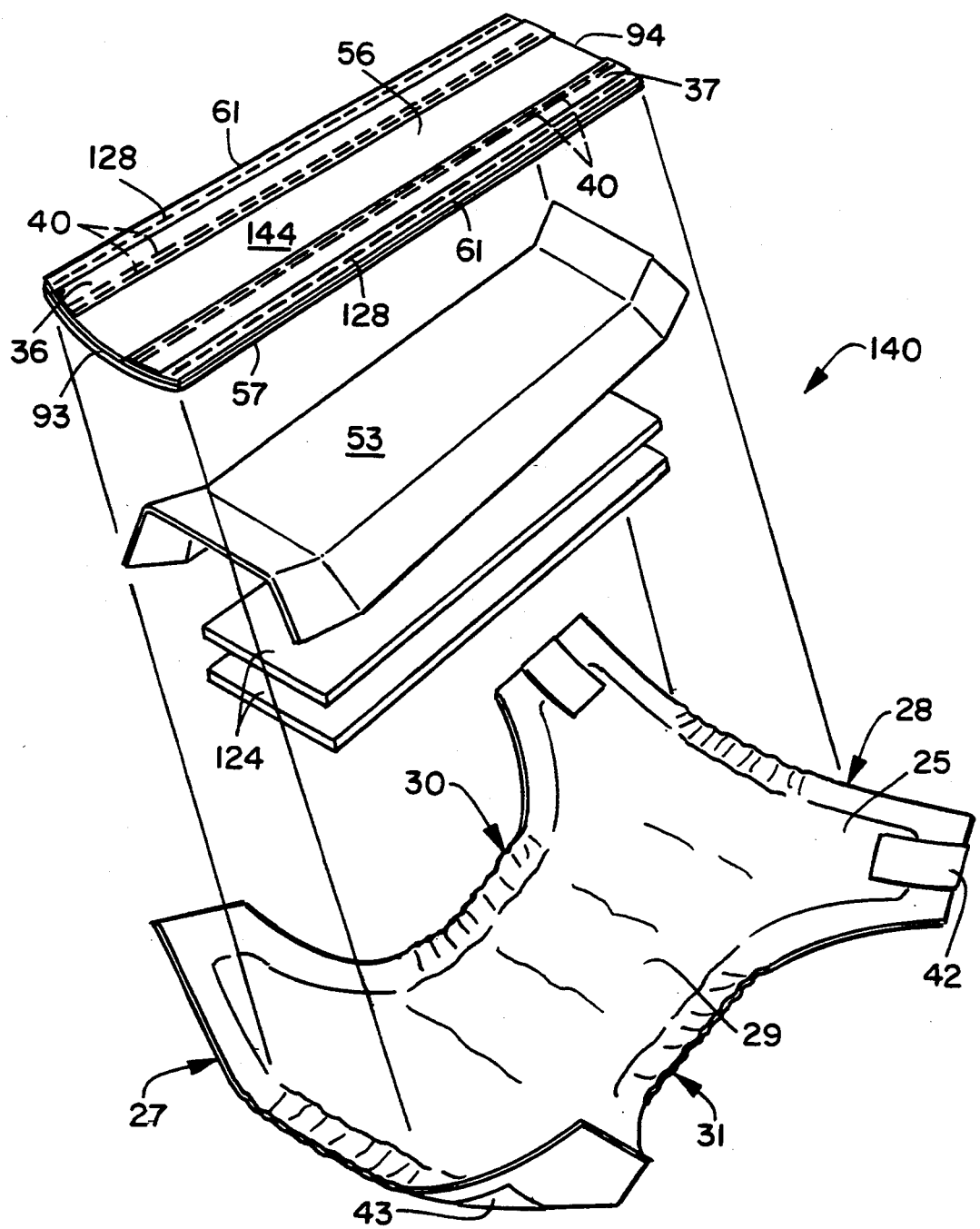
FIG. 14 is an exploded perspective view of a sixth embodiment of an absorbent article according to the present invention.
Figure 15:
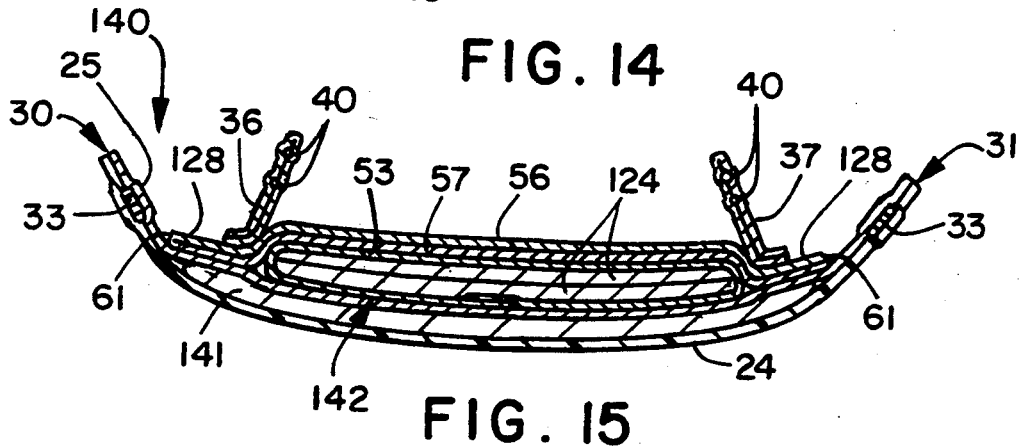
FIG. 15 is an enlarged view in section, similar to FIG. 4, but relating to the absorbent article of FIG. 14, with several components disproportionately enlarged for the purposes of illustration.

A sixth embodiment of the invention is illustrated by the diaper 140 in FIGS. 14 and 15, shown not to scale for purposes of clarity. This diaper 140 includes a relatively thin secondary absorbent body 141 that is sandwiched between the backing sheet 24 and the bodyside liner 25. The secondary absorbent body 141 is formed of a relatively thin absorbent material, which may include wood pulp fluff, coform material, and high-absorbency materials. The secondary absorbent body 141 is formed with an hourglass or I shape, and does not include a pocket as employed with several previous embodiments disclosed herein.

A flushable, absorbent insert pad 142 of the diaper 140 comprises an absorbent material, in the form of pair of thin absorbent sheets 124, which are wrapped in a carrier sheet 53. Two thin absorbent sheets 124 are illustrated in FIGS. 14 and 15, although the number may be varied to obtain the required level of absorbent capacity. Tissue sheets (not shown) may also be employed in contact with the thin absorbent sheets to contain the high-absorbency materials and help distribute fluids. The ends of the carrier sheet 53 may be bonded together by sonic bonds, adhesives or other suitable means to retain the thin absorbent sheets 124 within the carrier sheet 53, but are preferably bonded using a binder that will rapidly break down when immersed in toilet bowl water. The absorbent insert pad 142 is a full-length pad but could optionally be formed as a partial-length pad.

The diaper 140 includes a cover 144 having exposed front and back edges 93 and 94 and longitudinally-extending sides 61 extending between the front and back edges. The cover is formed with a top insert liner 56 and a bottom transfer layer 57, but could optionally be formed as a single layer or include a surge layer 127. Inboard of the longitudinal sides 61, the cover 144 includes two longitudinally-extending lines of relative weakness in the form of lines of perforations 128 that extend the complete length of the cover. Inboard of the perforations 128, containment flaps 36 and 37 are attached to or formed from the cover 144.

The insert pad 142 is positioned on the bodyside liner 25, centered between the side sections 30 and 31. In this diaper 140, the absorbent material of the insert pad 142 is in substantially direct fluid contact with the secondary absorbent body 141, whereby fluid can migrate along the most direct line from any given portion of the absorbent material of the pad 142 to the secondary absorbent body 141 without encountering a substantially liquid impervious material, such as a portion of the backing sheet 24. Specifically, only the carrier sheet 53 and the bodyside liner 25, which are both substantially liquid pervious, separate the absorbent material of the insert pad 142 and the secondary absorbent body 141.

The cover 144 is positioned over the insert pad 142 and the longitudinally-extending sides 61 are attached to the bodyside liner 25 using ultrasonic bonds, adhesives or other suitable means. The components of the diaper 140 are preferably sized so that the containment flaps 36 and 37 are outboard of the absorbent insert pad 142.

The absorbent insert pad 142 may be removed from the diaper 140 by pulling on either the exposed front edge 93 or the exposed back edge 94 of the cover 144. The cover 144 will thereby tear along the lines of perforations 128 to expose the absorbent insert pad 142 which lies beneath the cover. In this embodiment, the containment flaps 36 and 37 remain attached to the portion of the cover 144, between the lines of perforations 128, that is separated from the shell of the diaper. Advantageously, solid fecal waste on the cover 144 tends to be held in place between the elastic containment flaps 36 and 37 as the cover is being removed. Such fecal material can then be deposited in a toilet by completely removing the cover 144 and rinsing it in the toilet.

This diaper 140 is also advantageous because of its relative thinness, which is attributable to the thin absorbent sheets 124 and the relatively thin secondary absorbent body 141. The diaper 140 also provides manufacturing efficiencies because the secondary absorbent body 141 does not need to be formed with a pocket or C-shaped portions. Furthermore, because the absorbent material 124 is in substantially direct fluid contact with the secondary absorbent body 141, the secondary absorbent body can rapidly absorb liquid from the insert pad before the insert pad becomes saturated. This enhances the performance of the diaper 140 by attracting liquid away from the cover 144, thereby keeping it dry and comfortable. Complete direct fluid contact between the absorbent material 124 and the secondary absorbent body 141 is not required, because relatively small pieces of liquid impervious material, such as tapes, elastics, or other materials, positioned between the absorbent material of the insert pad 142 and the secondary absorbent body will not substantially impede fluid movement from the insert pad 142 to the secondary body.

It will be apparent to one skilled in the art that the cover 144 could be extended to be substantially coterminous with the backing sheet 24 (not shown). In this case, the cover would function as a cover/bodyside liner. In such an article, the absorbent insert pad 142 could be positioned beneath the cover/bodyside liner, and the cover/bodyside liner could be formed with one or more lines of relative weakness, such as perforations 128. The insert pad 142 could be released from beneath the cover/bodyside liner by tearing the cover/bodyside liner along the lines of relative weakness (perforations 128).

The foregoing detailed description has been for the purpose of illustration. Thus, a number of modifications and changes may be made without departing from the spirit and scope of the present invention. For example, the relative size of the pocket 47 and cover 23 may be modified to comprise a greater or lesser area of the article. Also, alternative absorbent materials may be substituted for those described herein. Likewise, presently non-flushable components, such as the cover 23, may be formed of flushable materials and discarded into the toilet with the flushable insert pad. Further, many of the particular aspects described in relation to one embodiment may be implemented in combination with aspects of other embodiments. Such aspects include: the design of the secondary absorbent layer, the absorbent insert pad, or the cover; the location of the containment flaps; and the use of perforation lines or a partial or a full-length insert pad. Therefore, the invention should not be limited by the specific embodiments described, but only by the claims.

We claim:

1. An absorbent article having a longitudinal axis, comprising;

a shell having a top surface and an opposite bottom surface and defining a front waist section, a back waist section, and opposed first and second sides extending between the front and back waist sections;

a pair of elasticized containment flaps extending between the front and back waist sections and being positioned inboard of the respective first and second sides;

an insert pad formed of a flushable absorbent material, the insert pad positioned against the top surface of the shell and located generally between the containment flaps; and a cover having opposite front and back edges and longitudinal sides extending between the front and back edges, the cover being positioned over the insert pad and the longitudinal sides being attached to the top surface of the shell, the cover having longitudinally-extending lines of relative weakness with respect to other portions of the cover formed therein inboard of the longitudinal sides, the containment flaps being spaced inboard of the lines of relative weakness;

whereby the cover may be torn along the lines of relative weakness to expose the insert pad.

2. The absorbent article of claim 1, wherein the insert pad is formed with a tab positioned adjacent the front waist section.

3. The absorbent article of claim 1, further comprising a secondary absorbent layer located between the top and bottom surfaces of the shell.

4. The absorbent article of claim 3, wherein the flushable absorbent material is in substantially direct fluid contact with the secondary absorbent layer.

5. The absorbent article of claim 1, wherein the insert pad includes a flushable carrier sheet that covers the flushable absorbent material, the carrier sheet having opposite ends and sides that extend between the ends, the sides overlapping one another and being unbonded.

6. The absorbent article of claim 1, wherein the insert pad includes wood pulp fluff and at least about 20 weight percent high-absorbency material.

7. The absorbent article of claim 6, wherein the insert pad includes at least about 50 weight percent high-absorbency material.

8. An absorbent article having a longitudinal axis, comprising:

a shell having a top surface and an opposite bottom surface and defining a front waist section, a back waist section, and opposed first and second sides extending between the front and back waist sections;

an insert pad formed of an absorbent material and adapted to be flushed down a toilet, the insert pad positioned against the top surface of the shell; and a cover positioned over the insert pad, the cover having front and back edges and longitudinal sides extending between the front and back edges, the longitudinal sides attached to the top surface of the shell, the cover having longitudinally-extending lines of relative weakness with respect to other portions of the cover formed therein inboard of the longitudinal sides and elasticized containment flaps attached to the cover inboard of the lines of relative weakness;

whereby the cover may be torn along lines of relative weakness to expose the insert pad.

9. An absorbent article having a longitudinal axis, comprising:

a shell including a first sheet of a substantially liquid pervious material and a second sheet of a substantially liquid impervious material, the shell defining a front waist section, a back waist section, and opposed sides extending between the front and back waist sections, the first sheet being at least partially attached to the second sheet and including longitudinally-extending lines of relative weakness with respect to other portions of the first sheet, the lines of relative weakness located inboard of the sides;

an insert pad formed of a flushable absorbent material, the insert pad positioned within the shell between the first and second sheets and adjacent the lines of relative weakness; and a pair of elasticized containment flaps attached to the first sheet outboard of the insert pad and inboard of the lines of relative weakness;

wherein the insert pad is removable from within the shell upon severing the first sheet along the lines of relative weakness.

10. The absorbent article of claim 9, further comprising a secondary absorbent body disposed between the insert pad and the second sheet.

11. The absorbent article of claim 10, wherein the flushable absorbent material is in substantially direct fluid contact with the secondary absorbent body.

12. The absorbent article of claim 9, wherein the insert pad includes an absorbent material that is wrapped in a flushable carrier sheet.

13. The absorbent article of claim 12, wherein ends of the carrier sheet are folded onto themselves and boned together using a binder that rapidly breaks down in the presence of toilet bowl water.

14. An absorbent article having a longitudinal axis, comprising:

a shell having a top surface and an opposite bottom surface and defining a front waist section, a back waist section, and opposed first and second sides extending between the front and back waist sections;

an absorbent body disposed between the top and bottom surfaces of the shell;

an insert pad formed of an absorbent material and adapted to be flushed down a toilet, the insert pad positioned against the top surface of the shell, the absorbent material of the insert pad being in substantially direct fluid contact with the absorbent body; and a cover positioned over the insert pad, the cover having front and back edges and longitudinal sides extending between the front and back edges, the cover including longitudinally-extending lines of relative weakness with respect to the other portions of the cover formed therein inboard of longitudinal sides and elasticized containment flaps inboard of the lines of relative weakness;

whereby the cover may be torn along the lines of relive weakness to expose the insert pad.

15. The absorbent article of claim 14, wherein the insert pad is formed of an absorbent material that is wrapped in a flushable, dispersible carrier sheet.

16. The absorbent article of claim 14, wherein the absorbent material includes at least about 20 weight percent high-absorbency material.

17. The absorbent article of claim 16, wherein the absorbent material includes at least about 50 weight percent high-absorbency material.

18. An absorbent article having a longitudinal axis, comprising:
- a shell having a top surface and an opposite bottom surface and defining a front waist section, a back waist section, and opposed first and second sides extending between the front and back waist sections;
- an absorbent body disposed between the top and bottom surfaces of the shell;
- an insert pad formed of an absorbent material and adapted to be flushed down a toilet, the insert pad positioned against the top surface of the shell, the absorbent material of the insert pad being in substantially direct fluid contact with the absorbent body; and
- means for releasably maintaining the insert pad in contact with the top surface of the shell, wherein the means for releasably maintaining the insert pad comprises a cover attached to the top surface, the cover having front and back edges and longitudinal sides extending between the front and back edges, the cover including two longitudinally-extending lines of relative weakness with respect to other portions of the cover formed therein inboard of the longitudinal sides, the cover also including a pair of containment flaps attached to the cover inboard of the lines of relative weakness;
- whereby the cover may be torn along the lines of relative weakness to, expose the insert pad.

* * * * *